United States Patent [19]

Meyer et al.

[11] Patent Number: 4,621,082
[45] Date of Patent: Nov. 4, 1986

[54] PYRIDOPYRIMIDINES, PHARMACEUTICAL COMPOSITIONS AND USE

[75] Inventors: Horst Meyer; Egbert Wehinger, both of Wuppertal; Bernward Garthoff, Hilden; Stanislav Kazda, Wuppertal, all of Fed. Rep. of Germany

[73] Assignee: Bayer Aktiengesellschaft, Leverkusen, Fed. Rep. of Germany

[21] Appl. No.: 816,594

[22] Filed: Jan. 7, 1986

[30] Foreign Application Priority Data

Jan. 19, 1985 [DE] Fed. Rep. of Germany ....... 3501696

[51] Int. Cl.$^4$ ................. A61K 31/505; A61K 31/535; C07D 471/04
[52] U.S. Cl. .................................... 514/212; 514/222; 514/228; 514/229; 514/230; 514/231; 514/232; 514/234; 514/236; 514/238; 514/239; 514/240; 514/252; 514/258; 514/259; 544/58.6; 544/117; 544/238; 544/279; 544/80
[58] Field of Search ..................... 544/58.6, 117, 238, 544/279, 80; 514/212, 222, 228, 229, 230, 231, 232, 234, 236, 238, 239, 240, 252, 258, 259; 260/243.3

[56] References Cited

U.S. PATENT DOCUMENTS 3,505,332 4/1970 Hurlbert et al. ................... 544/279

Primary Examiner—Robert W. Ramsuer
Attorney, Agent, or Firm—Sprung, Horn, Kramer & Woods

[57] ABSTRACT

Pyridopyrimidines of the formula

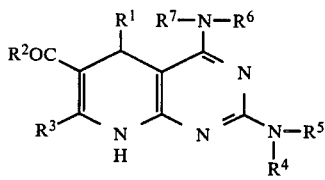

in which
$R^1$ is optionally substituted aryl or heterocyclic,
exhibit circulation active properties, especially renal vasodilating and diuretic action.

12 Claims, No Drawings

PYRIDOPYRIMIDINES, PHARMACEUTICAL COMPOSITIONS AND USE

The present invention relates to new pyridopyrimidines, several processes for their preparation and to their use as medicaments, in particular in agents acting on the circulation.

It has already been disclosed that derivatives of 1,2,3,7-tetrahydro-8-(2-imidazolin-2-yl)-imidazo[1,2-a]pyridine are obtained when equimolar quantities of an aldehyde and of a β-dicarbonyl compound are reacted with the hydrochloride of 2,2'-methylenediimidazoline (H. Meyer, Liebigs Ann. Chem. 1981, 1523).

The subject of the present invention is new pyridopyrimidines of the general formula I

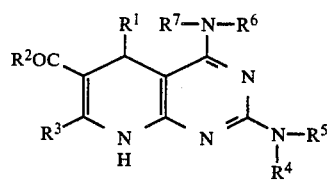

in which
$R^1$ represents carbocyclic aryl or a heterocyclic radical from the group comprising thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzthiadiazolyl, quinolyl, isoquinolyl, quinazolyl and quinoxalyl, the aryl radical and the heterocyclic radicals optionally containing 1 to 5 identical or different substituents from the group comprising phenyl, alkyl, alkoxy, alkylene, dioxyalkylene, halogen, polyfluoroalkyl, polyfluoroalkoxy, alkylamino, nitro, cyano, azido, alkoxycarbonyl, carbamoyl, sulphamoyl, $SO_m$-alkyl (m=0 to 2) and $SO_m$-aralkyl (m=0 to 2), $R^2$ represents a straight-chain, branched or cyclic alkyl radical or an aryl or aralkyl group, or denotes an amino, monoalkylamino or dialkylamino group, it being possible for the alkyl groups to be optionally substituted by a phenyl radical, or represents an anilino radical optionally substituted by alkyl, alkoxy or halogen, or represents the radical $OR^8$, in which $R^8$ represents a straight-chain, branched or cyclic, saturated or unsaturated hydrocarbon radical which is optionally interrupted by an oxygen or sulphur atom in the chain and/or is optionally substituted by halogen, cyano, hydroxyl, acyloxy, nitro, nitrooxy, alkoxycarbonyl, phenyl, phenoxy, phenylthio, phenylsulphonyl, pyridyl or an amino group, this amino group being optionally substituted by two identical or different substituents from the group comprising alkyl, alkoxyalkyl, aryl and aralkyl, or the amino group optionally being substituted in such a way that 2 substituents, together with the nitrogen atom, form a 5-membered to 7-membered ring which can contain oxygen or sulphur as a further hetero-atom or an N-alkyl/phenyl grouping, $R^3$ represents hydrogen, a straight-chain, branched or cyclic hydrocarbon radical optionally substituted by 1 or 2 alkoxy or acyloxy groups, or an aryl or aralkyl radical, and $R^4$, $R^5$, $R^6$ and $R^7$, which can be identical or different, represent hydrogen or a straight-chain or branched alkyl radical optionally substituted by hydroxyl, alkoxy or acyloxy, it being possible for the radicals $R^4$ and $R^5$ and/or $R^6$ and $R^7$, together with the respective nitrogen atom, to form a 5-membered to 7-membered ring which optionally contains oxygen or sulphur as a further hetero-atom or an N-alkyl or N-aryl grouping, or represents an aryl or aralkyl radical.

It has been found that the pyridopyrimidines according to the invention, of the general formula 1, are obtained when (A) ylidene-β-dicarbonyl compounds of the general formula II

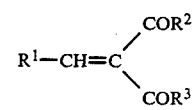

in which
$R^1$, $R^2$ and $R^3$ have the meaning given above,
are reacted with 6-aminopyrimidines of the general formula III

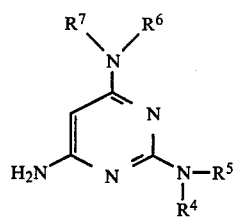

in which
$R^4$, $R^5$, $R^6$ and $R^7$ have the meaning given above,
optionally in the presence of organic solvents, or
(B) aldehydes of the general formula IV

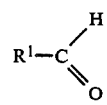

in which
$R^1$ has the meaning given above,
are reacted with β-dicarbonyl compounds of the general formula V

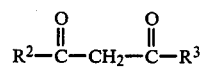

in which
$R^2$ and $R^3$ have the meaning given above,
and 6-aminopyrimidines of the general formula III

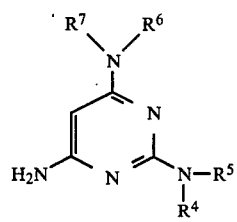

in which
$R^4$, $R^5$, $R^6$ and $R^7$ have the meaning given above,
optionally in the presence of organic solvents.

The pyridopyrimidines according to the invention, of the general formula I, are new and possess valuable pharmacological properties. Due to their action on the circulation, and their renal vasodilating and diuretic action, they can be used as antihypertensive agents, as vasodilators and as diuretics in the case of various disturbances of the circulation and of the electrolyte balance, and are thus to be regarded as an enrichment of pharmacy.

Due to the basic functions, the compounds according to the invention can be obtained as salts, depending on the preparation process. Both the free bases and the salts of the pyridopyrimidines of the general formula I are subjects of the present invention.

Depending on the nature of the starting materials used, the synthesis of the compounds according to the invention can be represented by the following equations, the preparation of isobutyl 2,4-diamino-7-methyl-5-(2-nitrophenyl)-5,8-dihydro-pyrido[2,3-d]pyrimidine-6-carboxylate and of ethyl 2,4-dimorpholino-7-methyl-5-(3-trifluoromethylphenyl)-5,8-dihydro-pyrido[2,3-d]pyrimidine-6-carboxylate being chosen as examples:

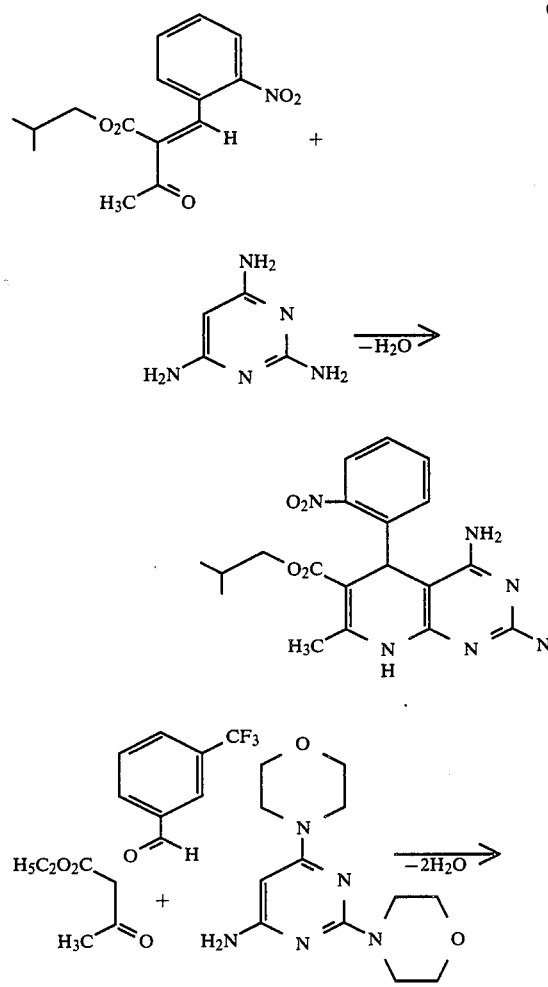

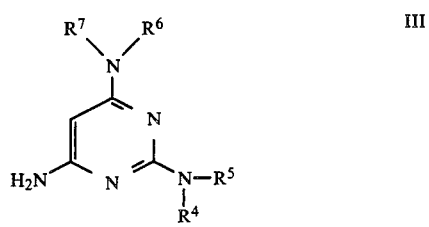

PROCESS VARIANT A

According to process A, an ylidene-$\beta$-dicarbonyl compound of the general formula II

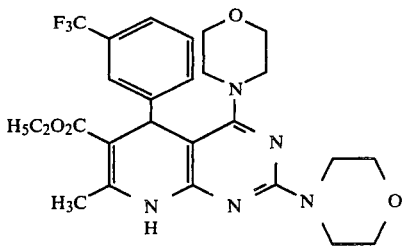

is reacted with 6-aminopyrimidine of the general formula III

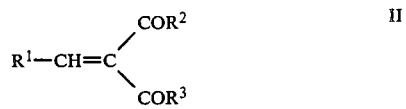

In the formulae I and II, $R^1$ preferably represents a phenyl or naphthyl radical or thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzthiadiazolyl, quinolyl, isoquinolyl, quinazolyl or quinoxalyl, it being possible for the heterocyclic radicals mentioned and the phenyl radical and the naphthyl radical each to carry 1 to 5 identical or different substituents, for which phenyl, straight-chain or branched alkyl having up to 8 carbon atoms, cycloalkyl having 3 to 7 carbon atoms, alkenyl or alkinyl having 2 to 6 carbon atoms, alkoxy having 1 to 4 carbon atoms, alkenoxy and alkinoxy having 2 to 6 carbon atoms, tri-, tetra- and pentamethylene, dioxymethylene, dioxyethylidene, halogen, such as fluorine, chlorine, bromine or iodine, trifluoromethyl, trifluoroethyl, trifluoromethoxy, difluoromethoxy, tetrafluoroethoxy, dialkylamino having 1 to 4 C atoms, nitro, cyano, azido, alkoxycarbonyl having 1 to 4 C atoms in the alkoxy radical, carbamoyl, N,N-dimethylcarbamoyl, sulphamoyl, $SO_m$-alkyl, in which m denotes 0 to 2 and alkyl contains 1 to 4 carbon atoms, or $SO_m$-benzyl with m=0 to 2 may be mentioned as substituents, $R^2$ preferably represents a straight-chain, branched or cyclic alkyl radical having up to 8 carbon atoms, or the phenyl or benzyl group or preferably represents the amino, monoamino or dialkylamino group having up to 4 carbon atoms per alkyl group, it being possible for one or both alkyl groups to be substituted by a phenyl radical, or preferably represents the anilino radical optionally substituted by fluorine or chlorine or by alkyl or alkoxy having 1 to 4 carbon atoms, or preferably represents the radical $OR^8$, in which $R^8$ represents a straight-chain, branched or cyclic, saturated or unsaturated hydrocarbon radical which has up to 12 carbon atoms and is optionally interrupted by 1 oxygen or sulphur atom in the chain and/or is optionally substituted by halogen, cyano, hydroxyl, acetoxy, benzoyloxy, nitro, nitrooxy, alkoxycarbonyl having up to 4 carbon atoms in the alkoxy group, phenyl, phenoxy, phenylthio, phenylsulphonyl, α-, β- or γ-pyridyl or an amino group, this amino group optionally carrying one or two identical or different substituents from the group comprising alkyl having 1 to 4 carbon atoms, alkoxyalkyl having up to 6 carbon atoms, phenyl, benzyl or phenethyl, or the nitrogen of this amino group, together with the substituents, optionally forming a 5-membered to 7-membered ring which can contain an oxygen or sulphur atom as a further hetero-atom or an N-phenyl group or an N-alkyl group having 1 to 4 carbon atoms in the alkyl radical, and $R^3$ preferably represents hydrogen or preferably represents a straight-chain, branched or cyclic hydrocarbon radical which has up to 6 carbon atoms and is optionally substituted by 1 or 2 alkoxy groups having 1 to 4 carbon atoms or by an acetoxy or benzoyloxy group, or preferably represents a phenyl radical or a benzyl radical.

The ylidene-β-dicarbonyl compounds of the formula II, used as starting materials, are known from the literature or can be prepared by methods known from the literature (compare, for example, G. Jones "The Knoevenagel Condensation" in Org. Reactions, Volume XV, 204 et seq. (1967)).

The following may be mentioned as examples: benzylideneacetylacetone, β,β-dibenzoylstyrene, 2'-nitrobenzylideneacetylacetone, 3'-nitrobenzylideneacetoacetanilide, 3'-nitrobenzylideneacetoacetamide, N,N-dimethyl-3'-nitrobenzylideneacetoacetamide, methyl 2'-nitrobenzylideneacetoacetate, decyl 3'-nitrobenzylideneacetoacetate, isopropyl 2'-trifluoromethylbenzylideneacetoacetate, cyclopentyl 2'-cyanobenzylideneacetoacetate, 2-methoxyethyl 2'-chlorobenzylideneacetoacetate, 2-cyanoethyl 2'-methoxybenzylideneacetoacetate, benzyl 2'-methylbenzylideneacetoacetate, pyrid-2-yl-methyl 3'-nitrobenzylideneacetoacetate, 2-(N-benzyl-N-methylamino)-ethyl 3'-nitrobenzylideneacetoacetate, 2-nitrooxyethyl 3'-nitrobenzylideneacetoacetate, propyl α-acetyl-β-(pyrid-3-yl)-acrylate, isobutyl α-acetyl-β-(pyrid-2-yl)-acrylate, 2-phenoxyethylα-acetyl-β-(quinolin-4-yl)-acrylate, methylα-acetyl-β-(2,1,3-benzoxadiazol-4-yl)-acrylate and isopropylα-propionyl-β-(2,1,3-benzothiadiazol-4-yl)-acrylate.

In the formulae I and III, $R^4$, $R^5$, $R^6$ and $R^7$, which can be identical or different, preferably represent hydrogen or preferably represent a straight-chain or branched alkyl radical which has up to 8 carbon atoms and is optionally substituted by hydroxyl, methoxy, acetoxy or benzoyloxy, it being possible for the radicals $R^4$ and $R^5$ and/or $R^6$ and $R^7$ together with the respective nitrogen atom to form a 5-membered to 7-membered ring which optionally contains oxygen or sulphur as a further hetero-atom or an N-alkyl group having up to 4 carbon atoms or an N-phenyl group, or preferably represents a phenyl or benzyl radical.

The 6-aminopyrimidines of the general formula III, used as starting materials, are known from the literature or can be prepared by methods known from the literature (compare, for example, Chem. Pharm. Bull. 19, 1526 (1971)).

The following may be mentioned as examples: 2,4,6-triaminopyrimidine, 6-amino-2,4-bis-(diethylamino)-pyrimidine, 6-amino-2,4-bis-(dibutylamino)-pyrimidine, 6-amino-2,4-bis-(di-(2-methoxyethyl)-amino)-pyrimidine, 6-amino-2,4-dimorpholino-pyrimidine, 6-amino-2,4-dithiomorpholino-pyrimidine, 6-amino-2,4-bis-(N-4-phenyl-piperazin-1-yl)-pyrimidine and 6-amino-2,4-bis-(N-4-benzyl-piperazin-1-yl)-pyrimidine.

The diluents which can be used are preferably organic solvents, such as, for example, alcohols such as methanol, ethanol or isopropanol, or ethers such as dioxane, tetrahydrofuran, glycol monomethyl ether or glycol dimethyl ether, or dimethylformamide, dimethyl sulphoxide, acetonitrile, pyridine or hexamethyl phosphoric acid triamide or glacial acetic acid.

The reaction temperatures can be varied within a fairly wide range. In general, the reaction is carried out between 20° C. and 150° C., preferably between 20° and 120° C., and in particular at the boiling point of the particular solvent.

The reaction can be carried out under normal pressure and also under an elevated pressure. In general, it is carried out under normal pressure.

When carrying out the process according to the invention, one mol of the ylidene compound is reacted with one mol of the 6-amino-pyrimidine derivative in a suitable solvent. The isolation and purification of the substances according to the invention are preferably carried out in such a way that the solvent is distilled off in vacuo and the residue obtained is recrystallized from a suitable solvent or subjected to one of the customary purification methods, such as, for example, column chromatography on suitable carrier materials.

PROCESS VARIANT B

According to process B, an aldehyde of the general formula IV

IV is reacted with a β-dicarbonyl compound of the general formula V

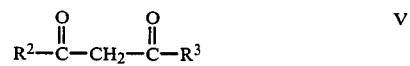

V and a 6-aminopyrimidine of the general formula III.

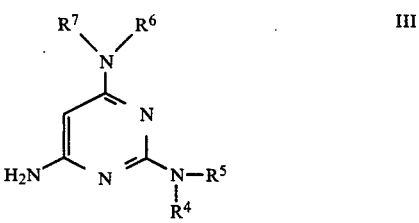

III

In the formulae IV, V and III, the radicals $R^1$, $R^2$, $R^3$, $R^4$, $R^5$, $R^6$ and $R^7$ have the meaning given above.

The aldehydes of the formula IV, which can be used as starting materials, are known from the literature or can be prepared by methods known from the literature (compare, for example, Mosettig, Org. Reactions VIII, 218 et seq. (1954)).

The following may be mentioned as examples: benzaldehyde, 2-, 3- or 4-phenylbenzaldehyde, α- or β-naphthylaldehyde, 2-, 3- or 4-methylbenzaldehyde, 2- or 4-n-butylbenzaldehyde, 2-, 3- or 4-isopropylbenzaldehyde, 2- or 4-cyclopropylbenzaldehyde, 2,3-tetramethylenebenzaldehyde, 3,4-dioxymethylenebenzaldehyde, 2-, 3- or 4-methoxybenzaldehyde, 2-, 3- or 4-chloro/bromo/fluorobenzaldehyde, 2-, 3- or 4-trifluoromethylbenzaldehyde, 2-, 3- or 4-trifluoromethoxybenzaldehyde, 2-, 3- or 4-difluoromethoxybenzaldehyde, 2-, 3- or 4-nitrobenzaldehyde, 2-, 3- or 4-cyanobenzaldehyde, 3-azidobenzaldehyde, 2-, 3- or 4-methylthiobenzaldehyde, 2-, 3- or 4-methylsulphinylbenzaldehyde, 2-, 3- or 4-methylsulphonylbenzaldehyde, 2,3-, 2,4- or 2,6-dichlorobenzaldehyde, 2-fluoro-3-chlorobenzaldehyde, 2,3,4,5,6-pentafluorobenzaldehyde, 2,4-dimethylbenzaldehyde, 2,4- or 2,6-dinitrobenzaldehyde, 2-chloro-6-nitrobenzaldehyde, 4-chloro-2-nitrobenzaldehyde, 2-nitro-4-methoxybenzaldehyde, 2-nitro-4-cyanobenzaldehyde, 2-chloro-4-cyanobenzaldehyde, 4-cyano-2-methylbenzaldehyde, 3-methyl-4-trifluoromethylbenzaldehyde, 3-chloro-2-trifluoromethylbenzaldehyde, thiophene-2-aldehyde, furan-2-aldehyde, pyrrole-2-aldehyde, pyrazole-4-aldehyde, imidazole-2-aldehyde, oxazole-2-aldehyde, isoxazole-3-aldehyde, thiazole-2-aldehyde, pyridine-2-, -3- or -4-aldehyde, 6-methyl-pyridine-2-aldehyde, 2-methylthio-pyridine-3-aldehyde, indole-3-aldehyde, benzimidazole-2-aldehyde, benzoxazole-4-aldehyde, benzoxadiazole-4-aldehyde, quinoline-4-aldehyde, quinazoline-2-aldehyde and quinoxaline-5-aldehyde.

The β-dicarbonyl compounds, which can be used according to the invention, of the general formula V are known from the literature or can be prepared by methods known from the literature (for example, D. Borrmann, "Umsetzung von Diketen mit Alkoholen, Phenolen und Mercaptanen [Reaction of diketene with alcohols, phenols and mercaptans]", in Houben-Weyl, Methoden der Organischen Chemie [Methods of Organic Chemistry], Volume VII/4, 230 et seq. (1968); Y. Oikawa, K. Sugano and O. Yonemitsu, J. Org. Chem. 43, 2087 (1978)).

The following may be mentioned as examples: acetylacetone, methyl acetoacetate, decyl acetoacetate, cyclopentyl acetoacetate, 2,2,2,-trifluoroethyl acetoacetate, 2-methoxyethyl acetoacetate, 2-phenoxyethyl acetoacetate, benzyl acetoacetate, 2-(N-benzyl-N-methylamino)-ethyl acetoacetate, 2-(pyrid-3-yl)-ethyl acetoacetate, 2-acetoxyethyl acetoacetate, 2-cyanoethyl acetoacetate, 2-nitrooxyethyl acetoacetate, acetoacetamide, N,N-dimethylacetoacetamide, acetoacetanilide, methyl propionylacetate and isobutyl benzoylacetate.

The 6-aminopyrimidines, employed as starting materials, of the general formula III have already been listed under process variant A.

The diluents which can be used are preferably organic solvents, such as, for example, alcohols such as methanol, ethanol or isopropanol, or ethers such as dioxane, tetrahydrofuran, glycol monomethyl ether or glycol dimethyl ether, or dimethylformamide, dimethyl sulphoxide, acetonitrile, pyridine, hexamethyl phosphoric acid triamide or glacial acetic acid.

The reaction temperatures can be varied within a fairly wide range. In general, the reaction is carried out between 20° C. and 150° C., preferably between 20° C. and 120° C., especially at the boiling point of the particular solvent.

The reaction can be carried out under normal pressure and also under an elevated pressure. In general, it is carried out under normal pressure.

When carrying out the process according to the invention, one mol of aldehyde is reacted with one mol of β-dicarbonyl compound and one mol of 6-aminopyrimidine. The isolation and purification of the substances according to the invention is preferably carried out in such a way that the solvent is distilled off in vacuo and the residue obtained is recrystallised from a suitable solvent or subjected to one of the purification methods known from the state of the art, such as, for example, column chromatography on suitable carrier materials.

The above preparation processes are indicated merely for clarification, and the preparation of the compounds of the formula (I) is not restricted to these processes, but any modification of these processes is applicable in the same way to the preparation of the compounds according to the invention.

Depending on the choice of the starting substances, the compounds according to the invention can exist in stereoisomeric formulae, which are either in a relationship of image and mirror image (enantiomers) or are not in a relationship of image and mirror image (diastereomers). The antipodes and the racemic forms and the diastereomer mixtures are all subjects of the present invention. The racemic forms can, like the diastereomers, be separated in a known manner into the single stereoisomeric constituents (compare, for example, E. L. Eliel, Stereochemistry of Carbon Compounds, McGraw Hill, 1962).

Of particular interest are compounds of the general formula (I) in which $R^1$ represents a phenyl or naphthyl radical or thienyl, furyl, pyridyl, pyridazinyl, pyrimidyl, benzoxadiazolyl, benzthiadiazolyl, quinolyl or isoquinolyl, it being possible for the said heterocyclic radicals and for the phenyl and naphthyl radical to carry 1 to 5 identical or different substituents from the group comprising straight-chain or branched alkyl having up to 8 carbon atoms, alkoxyalkyl having 1 to 4 carbon atoms, dioxymethylene, fluoro, chloro, bromo, trifluoromethyl, trifluoromethoxy, difluoromethoxy, nitro, cyano, azido, thioalkyl, sulphonylalkyl each having 1 to 4C atoms in the alkyl radical, thiobenzyl and sulphonylbenzyl, $R^2$ represents alkyl having up to 8C atoms, phenyl or benzyl, or represents the radical $OR^8$, in which $R^8$ represents a straight-chain, branched or cyclic, saturated or unsaturated hydrocarbon radical which has up to 12 carbon atoms and is optionally interrupted by 1 oxygen or sulphur atom in the chain and/or is optionally substituted by halogen, cyano, hydroxyl, acetoxy, phenyl, phenoxy, phenylthio, α-, β- or γ-pyridyl or an amino group, this amino group optionally carrying one or two identical or different substituents from the group comprising alkyl having 1 to 4C atoms, phenyl and benzyl, $R^3$ represents a straight-chain or branched hydrocarbon radical which has up to 6C atoms and is optionally substituted by 1 or 2 alkoxy groups having 1 to 4C atoms or by an acetoxy group, or represents a phenyl radical or benzyl radical and $R^4$, $R^5$, $R^6$ and $R^7$ each are identical or different and represent hydrogen or a straight-chain or branched alkyl radical which has up to 8 carbon atoms and is optionally substituted by hydroxyl, methoxy or acetoxy, it being possible for the radicals $R^4$ and $R^5$ and/or $R^6$ and $R^7$, together with the respective nitrogen atom, to form a 5-membered to 7-membered ring which optionally contains, as a further hetero-atom, oxygen, sulphur or an N-alkyl group having up to 4C atoms or an N-phenyl group.

In addition to the preparation examples given below, the following active compounds according to the invention may be mentioned:

ethyl 2,4-diamino-7-propyl-5-(3-nitrophenyl)-5,8-dihydropyrido[2,3-d]pyrimidine-6-carboxylate, methyl 2,4-diamino-7-phenyl-5-(2-chlorophenyl)-5,8-dihydropyrido[2,3-d]pyrimidine-6-carboxylate, methyl 2,4-diamino-7-benzyl-5-(2-trifluoromethylphenyl)-5,8-dihydro-pyrido[2,3-d]pyrimidine-6-carboxylate, isopropyl 2,4-diamino-7-methoxymethyl-5-(3-chlorophenyl)-5,8-dihydro-pyrido[2,3-d]pyrimidine-6-carboxylate, ethyl 2,4-bis(dibutylamino)-7-methyl-5-(2,3-dichlorophenyl)-5,8-dihydro-pyrido[2,3-d]pyrimidine-6-carboxylate, cyclopentyl 2,4-bis(dibutylamino)-7-ethyl-5-(2-trifluoromethylphenyl)-5,8-dihydro-pyrido[2,3-d]pyrimidine-6-carboxylate, decyl 2,4-bis(dibutylamino)-7-propyl-5-(3-nitrophenyl)-5,8-dihydro-pyrido[2,3-d]pyrimidine-6-carboxylate, isobutyl 2,4-dipiperidino-7-methyl-5-(2-nitrophenyl)-5,8-dihydro-pyrido[2,3-d]pyrimidine-6-carboxylate, 2-methoxyethyl 2,4-dipiperidino-7-phenyl-5-(2-chloro-3-trifluoromethylphenyl)-5,8-dihydro-pyrido[2,3-d]pyrimidine-6-carboxylate, isopropyl 2-morpholino-4-piperidino-7-methyl-5-(2-cyanophenyl)-5,8-dihydro-pyrido[2,3-d]pyrimidine-6-carboxylate, ethyl 2-morpholino-4-dimethylamino-7-methyl-5-(2,1,3-benzoxadiazol-4-yl)-5,8-dihydro-pyrido[2,3-d]pyrimidine-6-carboxylate, benzyl 2,4-dimorpholino-7-phenyl-5-(2,3-dichlorophenyl)-5,8-dihydro-pyrido[2,3-d]pyrimidine-6-carboxylate, 2,4-dimorpholino-7-benzyl-5-(2-chloro-3-nitrophenyl)-5,8-dihydro-pyrido[2,3-d]pyrimidine-6-carboxamide, N,N-dimethyl-5,8-dihydro-pyrido[2,3-d]pyrimidine-6-carboxamide and 2,4-dimorpholino-7-methyl-5-(pyrid-3-yl)-5,8-dihydropyrido[2,3-d]pyrimidine-6-carboxanilide.

Surprisingly, the compounds according to the invention exhibit special activities on the kidneys:

On anaesthetized dogs under artifical respiration, the compounds named above exert a specifically renal vasodilating effect which manifests itself in an increase of blood flow in the A. renalis. To establish the effect, the kidney arteries are exposed and surrounding tissue is removed. An electromagnetic "flow" measuring head is then fitted. The selective increase of flow in the renal arteries is observed after administration of doses of 0.03 mg/kg and higher of the compounds according to the invention. Effects on the general haemodynamics are detectable only at higher dosages of approximately 1 mg/kg and higher.

Furthermore, the compounds according to the invention have a diuretic activity which can be established on conscious rats after oral administration. For this purpose, conscious rats are stressed by means of 10 to 30 ml of water of 0.9% strength sodium chloride solution per kg of body weight, treated orally with solid substance taken up in Tylose suspension and then kept for 6 hours in metabolism cages for collecting the urine. In dosages of 3 mg/kg and higher perorally, the compounds indicated increase the urine volumes and the total of the electrolytes sodium and chloride excreted during this period. Compared with untreated control animals, the renal potassium excretion is only slightly increased.

The present invention also includes pharmaceutical formulations in dosage units. This means that the formulations are in the form of individual parts, for example tablets, dragees, capsules, pills, suppositories and ampules, of which the content of active compound correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and betonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, micro-crystalline cellulose, aluminum methanehydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutically active compounds in addition to the compounds of the above formula.

The abovementioned pharmaceutical formulations are prepared in the customary manner according to known methods, for example by mixing the active compound or compounds with the excipient or excipients.

The present invention also includes the use of the active compounds of the above formula, and of pharmaceutical formulations which contain one or more active compounds of the above formula, in human and veterinary medicine, for the prevention, alleviation and/or cure of the abovementioned diseases.

The active compounds or the pharmaceutical formulations can be administered orally, parenterally, intraperitoneally and/or rectally, preferably orally.

In general, it has proved advantageous, in intravenous administration, to administer the active compound or compounds in amounts of about 0.01 to about 20, preferably 0.1 to 10.0, mg/kg of body weight every 24 hours, distributed over 1 to 6 administrations. In oral administration, preferably 0.05 to 50 mg/kg, in particular 0.1 to 20 mg/kg, of body weight are given, namely before or/and during or/and after a meal. An individual dose contains the active compound or compounds preferably in quantities of about 0.01 to about 10.0 mg/kg of body weight. However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

PREPARATION EXAMPLES

Example 1

Ethyl 2,4-diamino-7-methyl-5-phenyl-5,8-dihydro-pyrido[2,3-d]pyrimidine-6-carboxylate

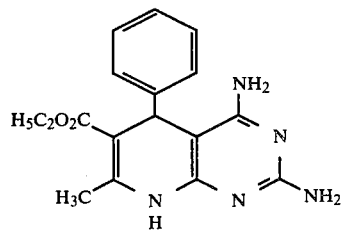

2.2 g (10 mmol) of ethyl 2-benzylideneacetoacetate were heated under reflux for 10 hours together with 1.3 g (10 mmol) of 2,4,6-triaminopyrimidine in 25 ml of glacial acetic acid. The reaction mixture was then cooled to room temperature, and the precipitated product was filtered off with suction and recrystallized as the acetate from acetonitrile.

Melting point: 145° C.
Yield: 2.8 g (73%).

Example 2

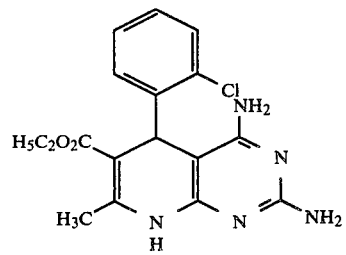

Analogously to Example 1, ethyl 2,4-diamino-7-methyl-5-(2-chlorophenyl)-5,8-dihydro-pyrido[2,3-d]pyrimidine-6-carboxylate was obtained as the acetate, melting point 150° C. (acetonitrile), by reacting ethyl 2-(2-chlorobenzylidene)-acetoacetate with 2,4,6-triaminopyrimidine. Yield: 60%.

Example 3

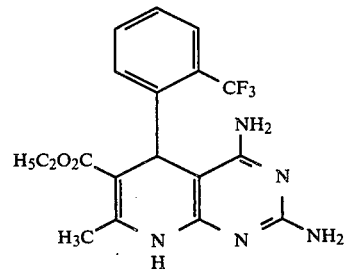

Analogously to Example 1, ethyl 2,4-diamino-7-methyl-5-(2-trifluoromethylphenyl)-5,8-dihydro-pyrido[2,3-d]pyrimidine-6-carboxylate was obtained as the acetate, melting point: 160° C. (isopropanol), by reacting ethyl 2-(2-trifluoromethylbenzylidene)-acetoacetate with 2,4,6-triaminopyrimidine. Yield: 58%.

Example 4

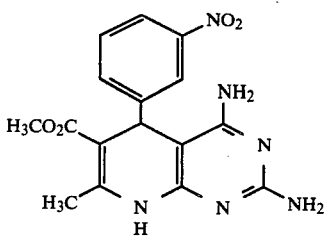

Analogously to Example 1, methyl 2,4-diamino-7-methyl-5-(3-nitrophenyl)-5,8-dihydro-pyrido[2,3-d]pyrimidine-6-carboxylate was obtained as the acetate, melting point: 250° C. (acetonitrile), by reacting methyl 2-(3-nitrobenzylidene)-acetoacetate with 2,4,6-triminopyrimidine. Yield: 73%.

Example 5

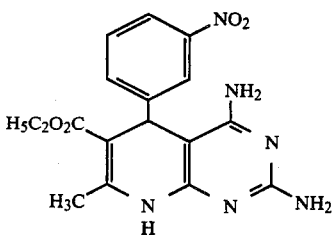

Analogously to Example 1, ethyl 2,4-diamino-7-methyl-5-(3-nitrophenyl)-5,8-dihydro-pyrido[2,3-d]pyrimidine-6-carboxylate of melting point: 230° C. (ethanol) was obtained by reacting ethyl 2-(3-nitrobenzylidene)-acetoacetate with 2,4,6-triaminopyrimidine. Yield: 78%.

Example 6

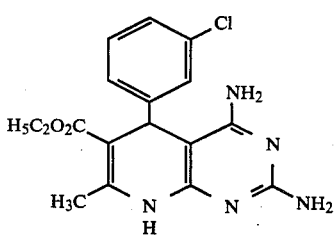

Analogously to Example 1, ethyl 2,4-diamino-7-methyl-5-(3-chlorophenyl)-5,8-dihydro-pyrido[2,3-d]pyrimidine-6-carboxylate was obtained as the acetate, melting point: 136° C. (acetonitrile), by reacting ethyl 2-(3-chlorobenzylidene)-acetoacetate with 2,4,6-triaminopyrimidine. Yield: 59%.

Example 7

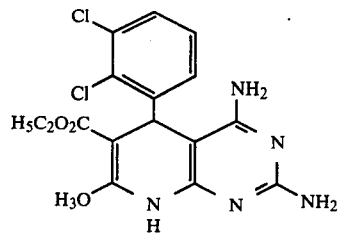

Analogously to Example 1, ethyl 2,4-diamino-7-methyl-5-(2,3-dichlorophenyl)-5,8-dihydro-pyrido[2,3-d]pyrimidine-6-carboxylate was obtained as the acetate, melting point: 177° C. (ethanol), by reacting ethyl 2-(2,3-dichlorobenzylidene)-acetoacetate with 2,4,6-triaminopyrimidine. Yield: 70%.

Example 8

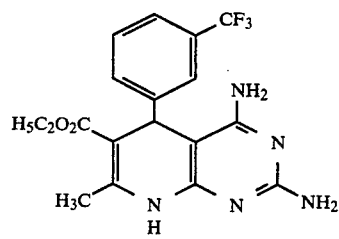

Analogously to Example 1, ethyl 2,4-diamino-7-methyl-5-(3-trifluoromethylphenyl)-5,8-dihydro-pyrido[2,3-d]pyrimidine-6-carboxylate was obtained as the diacetate of melting point: 123° C. (ethanol) by reacting ethyl 2-(3-trifluoromethylbenzylidene)-acetoacetate with 2,4,6-triaminopyrimidine in glacial acetic acid. Yield: 61%.

Example 9

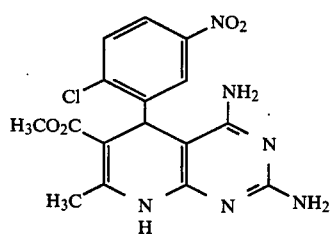

Analogously to Example 1, methyl 2,4-diamino-7-methyl-5-(2-chloro-5-nitrophenyl)-5,8-dihydro-pyrido[2,3-d]pyrimidine-6-carboxylate was obtained as the acetate of melting point: 282° C. (ethanol) by reacting methyl 2-(2-chloro-5-nitro-benzylidene)-acetoacetate with 2,4,6-triaminopyrimidine in glacial acetic acid. Yield: 55%.

Example 10

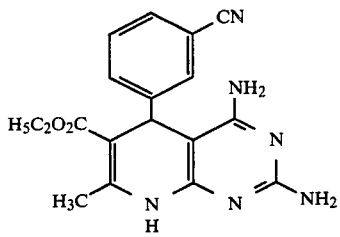

Analogously to Example 1, ethyl 2,4-diamino-7-methyl-5-(3-cyanophenyl)-5,8-dihydropyrido[2,3-d]pyrimidine-6-carboxylate was obtained as the acetate of melting point: 170° C. (acetonitrile) by reacting ethyl 2-(3-cyanobenzylidene)-acetoacetate with 2,4,6-triaminopyrimidine in glacial acetic acid. Yield: 61%.

Example 11

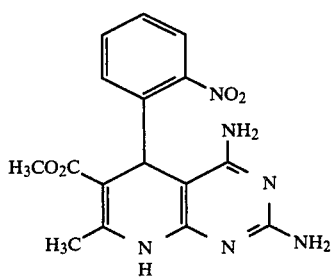

Analogously to Example 1, methyl 2,4-diamino-7-methyl-5-(2-nitrophenyl)-5,8-dihydro-pyrido[2,3-d]pyrimidine-6-carboxylate, melting point: 164° C. (ethanol), was obtained as the acetate by reacting methyl 2-(2-nitrobenzylidene)-aceto-acetate with 2,4,6-triaminopyrimidine in glacial acetic acid. Yield: 65%.

Example 12

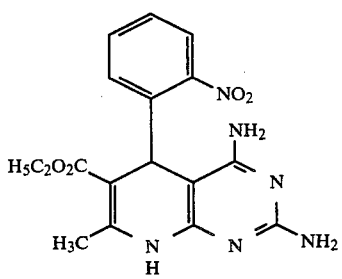

Analogously to Example 1, ethyl 2,4-diamino-7-methyl-5-(2-nitrophenyl)-5,8-dihydro-pyrido[2,3-d]pyrimidine-6-carboxylate was obtained as the acetate, melting point: 196° C. (ethanol), by reacting ethyl 2-(2-nitrobenzylidene)-acetoacetate with 2,4,6-triaminopyrimidine in glacial acetic acid. Yield: 67%.

Example 13

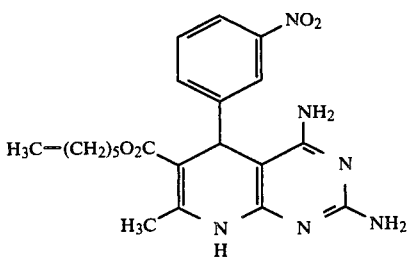

Analogously to Example 1, hexyl 2,4-diamino-7-methyl-5-(3-nitrophenyl)-5,8-dihydro-pyrido[2,3-d]pyrimidine-6-carboxylate was obtained as the diacetate, melting point: 132° C. (ethyl acetate), by reacting hexyl 2-(3-nitrobenzylidene)-acetoacetate with 2,4,6-triaminopyrimidine in glacial acetic acid. Yield: 59%.

Example 14

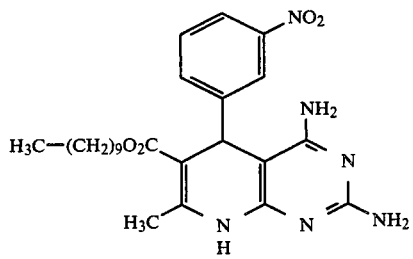

Analogously to Example 1, decyl 2,4-diamino-7-methyl-5-(3-nitrophenyl)-5,8-dihydro-pyrido[2,3-d]pyrimidine-6-carboxylate was obtained as the acetate of melting point: 103° C. (ethyl acetate) by reacting decyl 2-(3-nitrobenzylidene)-acetoacetate with 2,4,6-triaminopyrimidine in glacial acetic acid. Yield: 56%.

Example 15

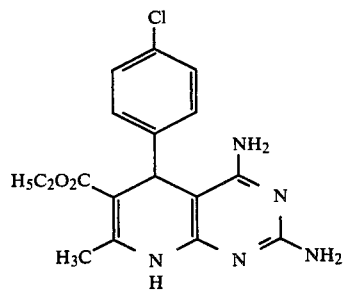

Analogously to Example 1, ethyl 2,4-diamino-7-methyl-5-(4-chlorophenyl)-5,8-dihydro-pyrido[2,3-d]pyrimidine-6-carboxylate was obtained as the half-acetate, melting point: 128° C. (isopropanol), by reacting ethyl 2-(4-chlorobenzylidene)-acetoacetate with 2,4,6-triaminopyrimidine in glacial acetic acid. Yield 75%.

Example 16

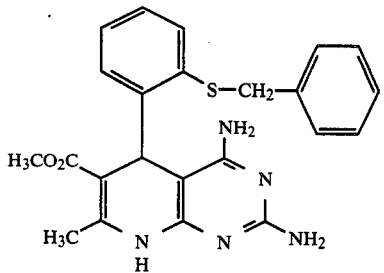

Analogously to Example 1, methyl 2,4-diamino-7-methyl-5-(2-benzylthiophenyl)-5,8-dihydro-pyrido[2,3-d]pyrimidine-6-carboxylate was obtained as the acetate of melting point: 139° C. (methanol) by reacting methyl 2-(2-benzylthiophenyl)-acetoacetate with 2,4,6-triaminopyrimidine in glacial acetic acid. Yield: 50%.

Example 17

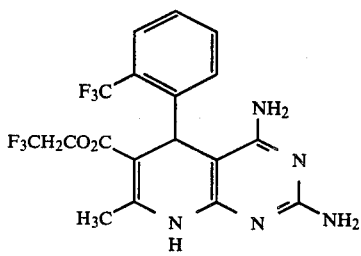

Analogously to Example 1, 2,2,2-trifluoroethyl 2,4-diamino-7-methyl-5-(2-trifluoromethylphenyl)-5,8-dihydro-pyrido[2,3-d]pyrimidine-6-carboxylate was obtained as the acetate, melting point: 145° C. (ethanol), by reacting 2,2,2-trifluoroethyl 2-(2-trifluoromethyl-benzylidene)-acetoacetate with 2,4,6-triaminopyrimidine in glacial acetic acid. Yield: 52%.

Example 18

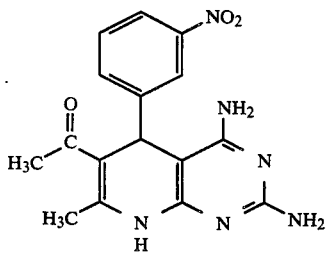

Analogously to Example 1, 6-acetyl-2,4-diamino-7-methyl-5-(3-nitrophenyl)-5,8-dihydro-pyrido[2,3-d]pyrimidine was obtained as the acetate of melting point: 260° C. (ethanol) by reacting 2-(3-nitrobenzylidene)-acetylacetone with 2,4,6-triaminopyrimidine in glacial acetic acid. Yield: 73%.

Example 19

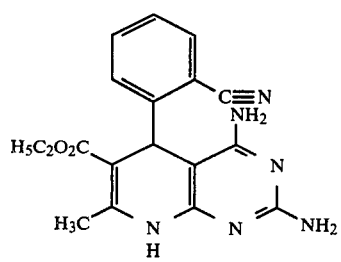

Analogously to Example 1, ethyl 2,4-diamino-7-methyl-5-(2-cyanophenyl)-5,8-dihydro-pyrido[2,3-d]pyrimidine-6-carboxylate was obtained as the acetate, melting point: 208° C. (ethanol), by reacting ethyl 2-(2-cyanobenzylidene)-acetoacetate with 2,4,6-triaminopyrimidine in glacial acetic acid. Yield: 59%.

Example 20

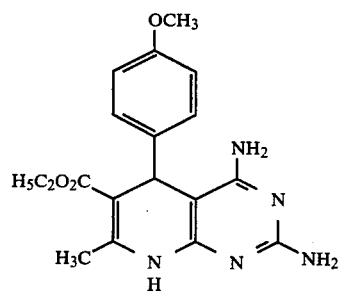

Analogously to Example 1, ethyl 2,4-diamino-7-methyl-5-(4-methoxyphenyl)-5,8-dihydro-pyrido[2,3-d]pyrimidine-6-carboxylate of melting point: 98° C. (ethyl acetate) was obtained by reacting ethyl 2-(4-methoxybenzylidene)-acetoacetate with 2,4,6-triaminopyrimidine in glacial acetic acid. Yield: 75%.

Example 21

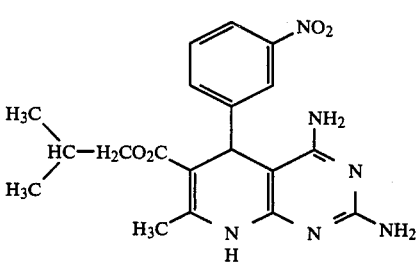

Analogously to Example 1, isobutyl 2,4-diamino-7-methyl-5-(3-nitrophenyl)-5,8-dihydro-pyrido[2,3-d]pyrimidine-6-carboxylate of melting point: 130° C. was obtained by reacting isobutyl 2-(3-nitrobenzylidene)-acetoacetate with 2,4,6-triaminopyrimidine in glacial acetic acid. Yield: 78%.

Example 22

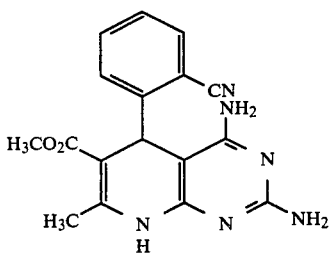

Analogously to Example 1, methyl 2,4-diamino-7-methyl-5-(2-cyanophenyl)-5,8-dihydro-pyrido[2,3-d]pyrimidine-6-carboxylate was obtained as the hald-acetate, melting point: 170° C. (methanol), by reacting methyl 2-(2-cyanobenzylidene)-acetoacetate with 2,4,6-triaminopyrimidine. Yield: 55%.

Example 23

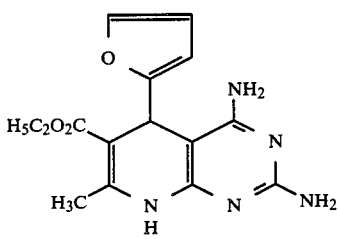

Analogously to Example 1, ethyl 2,4-diamino-7-methyl-5-(fur-2-yl)-5,8-dihydro-pyrido[2,3-d]pyrimidine-6-carboxylate was obtained as the acetate of melting point: 106° C. (acetonitrile) by reacting ethyl 2-acetyl-3-(fur-2-yl)-acrylate with 2,4,6-triaminopyrimidine in glacial acetic acid. Yield: 57%.

Example 24

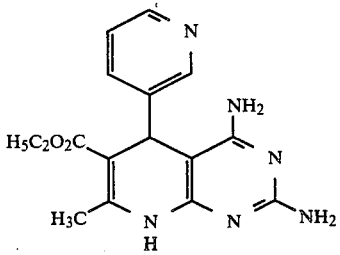

Analogously to Example 1, ethyl 2,4-diamino-7-methyl-5-(pyrid-3-yl)-5,8-dihydro-pyrido[2,3-d]pyrimidine-6-carboxylate of melting point: 224° C. (methanol) was obtained by reacting ethyl 2-acetyl-3-(pyrid-3-yl)-acrylate with 2,4,6-triaminopyrimidine in glacial acetic acid. Yield: 63%.

Example 25

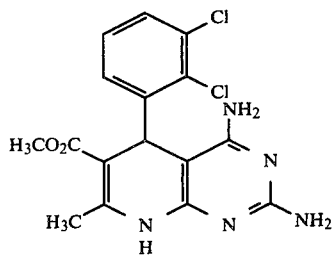

Analogously to Example 1, methyl 2,4-diamino-7-methyl-5-(2,3-dichlorophenyl)-5,8-dihydro-pyrido[2,3-d]pyrimidine-6-carboxylate was obtained as the acetate of melting point: 160° C. (ethanol) by reacting ethyl 2-(2,3-dichlorobenzylidene)-acetoacetate with 2,4,6-triaminopyrimidine in glacial acetic acid. Yield: 72%.

Example 26

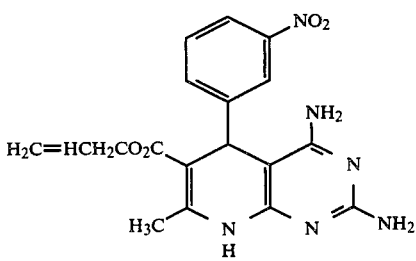

Analogously to Example 1, allyl 2,4-diamino-7-methyl-5-(3-nitrophenyl)-5,8-dihydro-pyrido[2,3-d]pyrimidine-6-carboxylate of melting point: 188° C. (ethyl acetate) was obtained by reacting allyl 2-(3-nitrobenzylidene)-acetoacetate with 2,4,6-triaminopyrimidine in glacial acetic acid. Yield: 64%.

Example 27

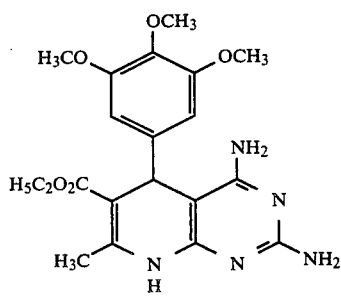

Analogously to Example 1, ethyl 2,4-diamino-7-methyl-5-(3,4,5-trimethoxyphenyl)-5,8-dihydro-pyrido[2,3-d]pyrimidine-6-carboxylate of melting point: 126° C. (ethyl acetate) was obtained by reacting ethyl 2-(3,4,5-trimethoxybenzylidene)-acetoacetate with 2,4,6-triaminopyrimidine in glacial acetic acid. Yield: 69%.

Example 28

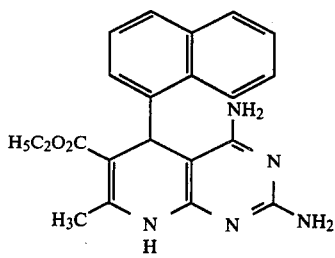

Analogously to Example 1, ethyl 2,4-diamino-7-methyl-5-(naphth-1-yl)-5,8-dihydro-pyrido[2,3-d]pyrimidine-6-carboxylate was obtained as the half-acetate of melting point: 209° C. (methanol) by reacting ethyl 2-acetyl-3-(naphth-1-yl)-acrylate with 2,4,6-triaminopyrimidine in glacial acetic acid. Yield: 35%.

Example 29

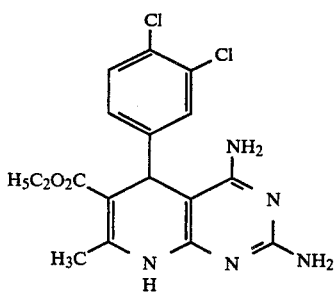

Analogously to Example 1, ethyl 2,4-diamino-7-methyl-5-(3,4-dichlorophenyl)-5,8-dihydro-pyrido[2,3-d]pyrimidine-6-carboxylate of melting point: 244° C. (ethanol) was obtained by reacting ethyl 2-(3,4-dichlorobenzylidene)-acetoacetate with 2,4,6-triaminopyrimidine in glacial acetic acid. Yield: 76%.

Example 30

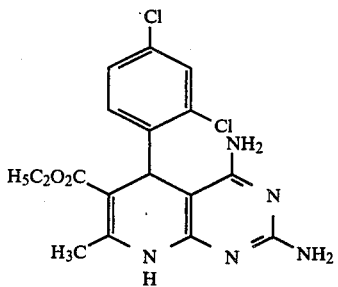

Analogously to Example 1, ethyl 2,4-diamino-7-methyl-5-(2,4-dichlorophenyl)-5,8-dihydro-pyrido[2,3-d]pyrimidine-6-carboxylate was obtained as the diacetate of melting point: 148° C. (ethanol) by reacting ethyl 2-(2,4-dichlorobenzylidene)-acetoacetate with 2,4,6-triaminopyrimidine in glacial acetic acid. Yield: 72%.

Example 31

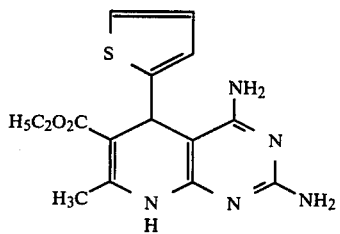

Analogously to Example 1, ethyl 2,4-diamino-7-methyl-5-(thien-2-yl)-5,8-dihydropyrido[2,3-d]pyrimidine-6-carboxylate was obtained as the diacetate, melting point: 126° C. (methanol), by reacting ethyl 2-acetyl-3-(thien-2-yl)-acrylate with 2,4,6-triaminopyrimidine in glacial acetic acid. Yield: 51%.

Example 32

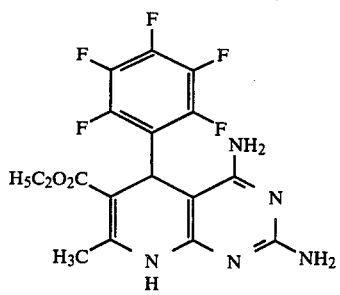

Analogously to Example 1, ethyl 2,4-diamino-7-methyl-5-(pentafluorophenyl)-5,8-dihydro-pyrido[2,3-d]pyrimidine-6-carboxylate was obtained as the triacetate of melting point: 162° C. (acetic acid) by reacting ethyl 2-(2,3,4,5,6-pentafluorobenzylidene)-acetoacetate with 2,4,6-triaminopyrimidine in glacial acetic acid. Yield: 37%.

Example 33

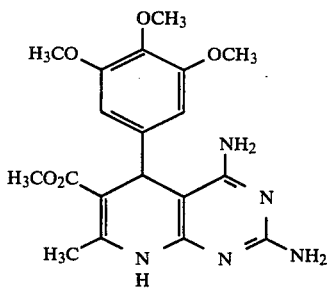

Analogously to Example 1, methyl 2,4-diamino-7-methyl-5-(3,4,5-trimethoxyphenyl)-5,8-dihydro-pyrido[2,3-d]pyrimidine-6-carboxylate was obtained as the acetate of melting point: 168° C. (water) by reacting methyl 2-(3,4,5-trimethoxybenzylidene)-acetoacetate with 2,4,6-triaminopyrimidine in glacial acetic acid. Yield: 72%.

Example 34

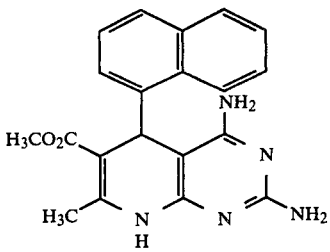

Analogously to Example 1, methyl 2,4-diamino-7-methyl-5-(naphth-1-yl)-5,8-dihydro-pyrido[2,3-d]pyrimidine-6-carboxylate was obtained as the acetate of melting point: 210° C. (ethyl acetate/methanol) by reacting methyl 2-acetyl-3-(naphth-1-yl)-acrylate with 2,4,6-triaminopyrimidine in glacial acetic acid. Yield: 36%.

Example 35

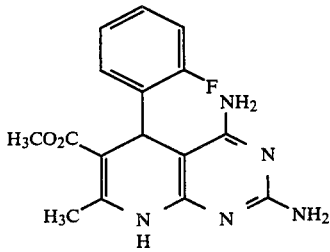

Analogously to Example 1, methyl 2,4-diamino-7-methyl-5-(2-fluorophenyl)-5,8-dihydro-pyrido[2,3-d]pyrimidine-6-carboxylate of melting point: 208° C. (isopropanol) was obtained by reacting methyl 2-(2-fluorobenzylidene)-acetoacetate with 2,4,6-triaminopyrimidine in glacial acetic acid. Yield: 76%.

Example 36

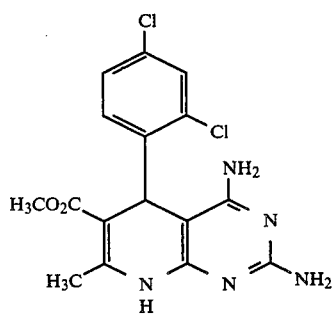

Analogously to Example 1, methyl 2,4-diamino-7-methyl-5-(2,4-dichlorophenyl)-5,8-dihydro-pyrido[2,3-d]pyrimidine-6-carboxylate was obtained as the acetate, melting point: 150° C. (ethanol), by reacting methyl 2-(2,4-dichlorobenzylidene)-acetoacetate with 2,4,6-triaminopyrimidine in glacial acetic acid. Yield: 71%.

Example 37

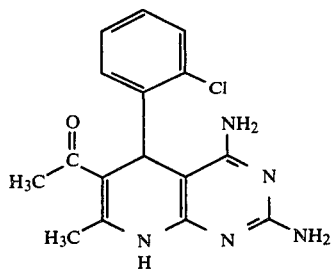

Analogously to Example 1, 6-acetyl-2,4-diamino-7-methyl-5-(2-chlorophenyl)-5,8-dihydro-pyrido[2,3-d]pyrimidine of melting point: 254° C. (ethyl acetate) was obtained by reacting 2-(2-chlorobenzylidene)-acetylacetone with 2,4,6-triaminopyrimidine in glacial acetic acid. Yield: 70%.

Example 38

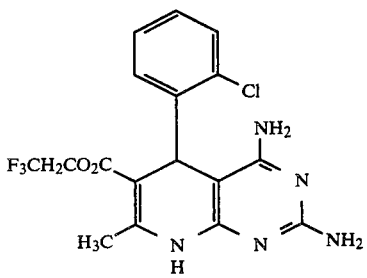

Analogously to Example 1, 2,2,2-trifluoroethyl 2,4-diamino-7-methyl-5-(2-chlorophenyl)-5,8-dihydropyrido[2,3-d]pyrimidine-6-carboxylate was obtained as the diacetate of melting point: 146° C. by reacting 2,2,2-trifluoroethyl 2-(2-chlorobenzylidene)-acetoacetate with 2,4,6-triaminopyrimidine in glacial acetic acid. Yield: 53%.

Example 39

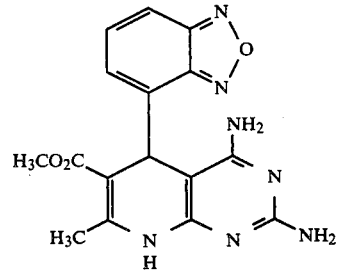

Analogously to Example 1, methyl 2,4-diamino-7-methyl-5-(2,1,3-benzoxadiazol-4-yl)-5,8-dihydro-pyrido[2,3d]pyrimidine-6-carboxylate of melting point: 268° C. (ethanol) was obtained by reacting methyl 2-acetyl-3-(2,1,3-benzoxadiazol-4-yl)-acrylate with 2,4,6-triaminopyrimidine in glacial acetic acid. Yield: 51%.

Example 40

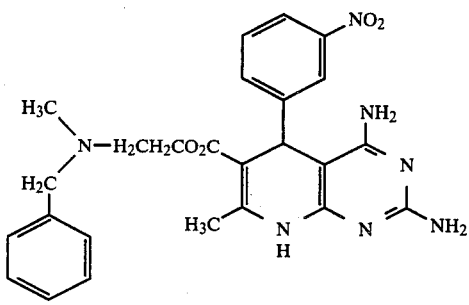

Analogously to Example 1, 2-(N-benzyl-N-methylamino)-ethyl 2,4-diamino-7-methyl-5-(3-nitrophenyl)-5,8-dihydro-pyrido[2,3-d]pyrimidine-6-carboxylate of melting point: 162° C. (ethyl acetate) was obtained by reacting 2-(N-benzyl-N-methylamino)-ethyl 2-(3-nitrobenzylidene)-acetoacetate with 2,4,6-triaminopyrimidine in glacial acetic acid. Yield: 53%.

Example 41

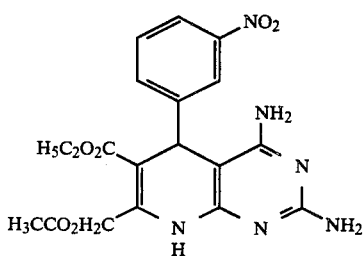

Analogously to Example 1, ethyl 7-acetoxymethyl-2,4-diamino-5-(3-nitrophenyl)-5,8-dihydro-pyrido[2,3-d]pyrimidine-6-carboxylate of melting point: 219° C. was obtained by reacting ethyl 4-acetoxy-2-(3-nitrobenzylidene)-acetoacetate with 2,4,6-triaminopyrimidine in glacial acetic acid. Yield: 65%.

Example 42

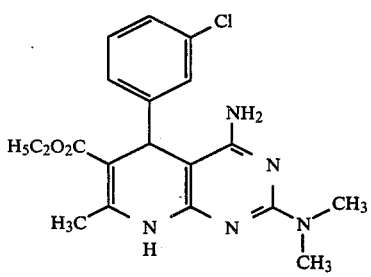

Analogously to Example 1, ethyl 4-amino-2-dimethylamino-7-methyl-5-(3-chlorophenyl)-5,8-dihydropyrido[2,3-d]pyrimidine-6-carboxylate of melting point: 214° C. (ethanol) was obtained by reacting ethyl 2-(3-chlorobenzylidene)-acetoacetate with 2-dimethylamino-4,6-diamino-pyrimidine in glacial acetic acid. Yield: 55%.

Example 43

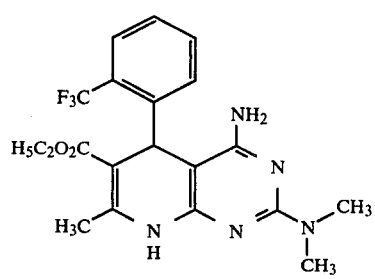

Analogously to Example 1, ethyl 4-amino-2-dimethylamino-7-methyl-5-(2-trifluoromethylphenyl)-5,8-dihydropyrido[2,3-d]pyrimidine-6-carboxylate of melting point: 210° C. (ethanol) was obtained by reacting ethyl 2-(2-trifluoromethylbenzylidene)-acetoacetate with 2-dimethylamino-4,6-diamino-pyrimidine in glacial acetic acid. Yield: 61%.

Example 44

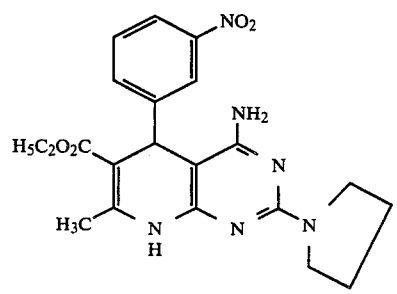

Analogously to Example 1, ethyl 4-amino-2-pyrrolidino-7-methyl-5-(3-nitrophenyl)-5,8-dihydro[2,3-d]pyrimidine-6-carboxylate was obtained as the diacetate, melting point: 243° C. (isopropanol), by reacting ethyl 2-(3-nitrobenzylidene)-acetoacetate with 2-pyrrolidino-4,6-diamino-pyrimidine in glacial acetic acid. Yield: 59%.

Example 45

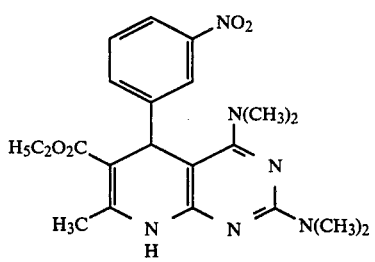

Analogously to Example 1, ethyl 2,4-bis-(dimethylamino)-7-methyl-5-(3-nitrophenyl)-5,8-dihydropyrido[2,3-d]pyrimidine-6-carboxylate of melting point: 149° C. (isopropanol) was obtained by reacting ethyl 2-(3-nitrobenzylidene)-acetoacetate with 6-amino-2,4-bis-(dimethylamino)-pyrimidine in glacial acetic acid. Yield: 55%.

Example 46

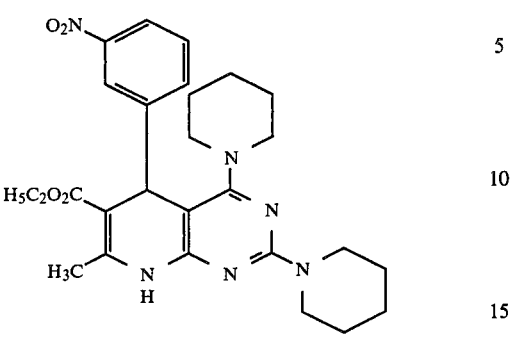

Analogously to Example 1, ethyl 2,4-dipiperidino-7-methyl-5-(3-nitrophenyl)-5,8-dihydro-pyrido[2,3-d]pyrimidine-6-carboxylate of melting point: 169° C. (ethanol/water) was obtained by reacting ethyl 2-(3-nitrobenzylidene)-acetoacetate with 6-amino-2,4-dipiperidino-pyrimidine in glacial acetic acid. Yield: 45%.

Example 47

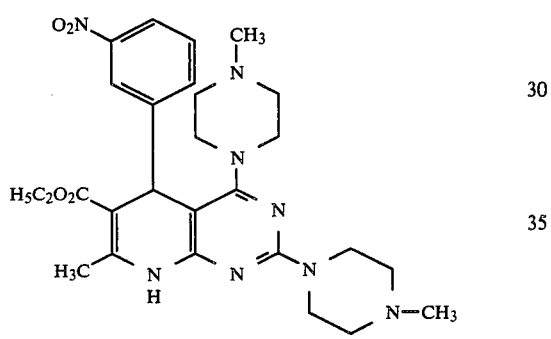

Analogously to Example 1, ethyl 2,4-bis-(N-4-methylpiperazin-1-yl)-7-methyl-5-(3-nitrophenyl)-5,8-dihydro-pyrido[2,3-d]pyrimidine-6-carboxylate of melting point: 140° C. (methanol) was obtained by reacting ethyl 2-(3-nitrobenzylidene)-acetoacetate with 6-amino-2,4-bis-(N-4-methylpiperazin-1-yl)-pyrimidine in glacial acetic acid. Yield: 43%.

Example 48

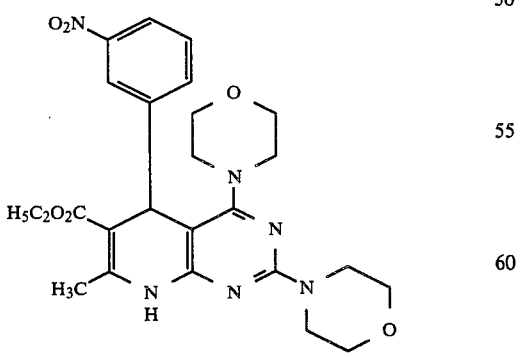

Analogously to Example 1, ethyl 2,4-dimorpholino-7-methyl-5-(3-nitrophenyl)-5,8-dihydro-pyrido[2,3-d]pyrimidine-6-carboxylate of melting point: 190° C. (ethanol) was obtained by reacting ethyl 2-(3-nitrobenzylidene)-acetoacetate with 6-amino-2,4-dimorpholino-pyrimidine in glacial acetic acid. Yield: 67%.

Example 49

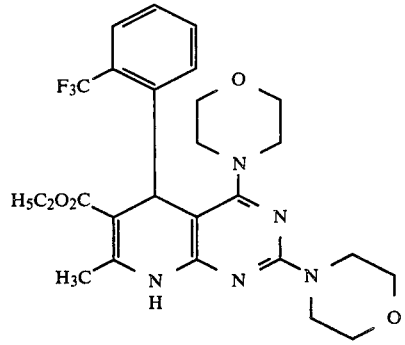

Analogously to Example 1, ethyl 2,4-dimorpholino-7-methyl-5-(2-trifluoromethylphenyl)-5,8-dihydro-pyrido[2,3-d]pyrimidine-6-carboxylate of melting point: 214° C. (isopropanol) was obtained by reacting ethyl 2-(2-trifluoromethylbenzylidene)-acetoacetate with 6-amino-2,4-dimorpholino-pyrimidine in glacial acetic acid. Yield: 66%.

Example 50

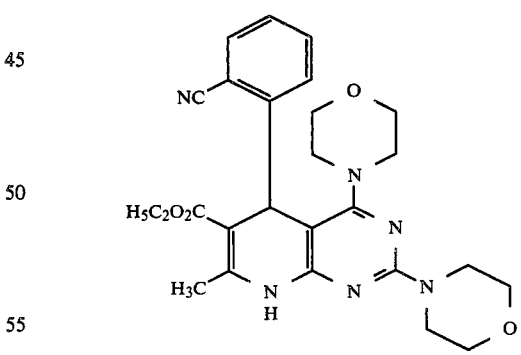

Analogously to Example 1, ethyl 2,4-dimorpholino-7-methyl-5-(2-cyanophenyl)-5,8-dihydro-pyrido[2,3-d]pyrimidine-6-carboxylate of melting point: 248° C. (isopropanol) was obtained by reacting ethyl 2-(2-cyanobenzylidene)-acetoacetate with 6-amino-2,4-dimorpholino-pyrimidine in ethanol. Yield: 75%.

Example 51

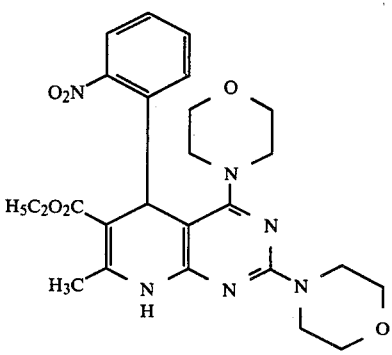

Analogously to Example 1, ethyl 2,4-dimorpholino-7-methyl-5-(2-nitrophenyl)-5,8-dihydro-pyrido[2,3-d]pyrimidine-6-carboxylate of melting point: 201° C. (isopropanol) was obtained by reacting ethyl 2-(2-nitrobenzylidene)-acetoacetate with 6-amino-2,4-dimorpholino-pyrimidine in ethanol. Yield: 65%.

Example 52

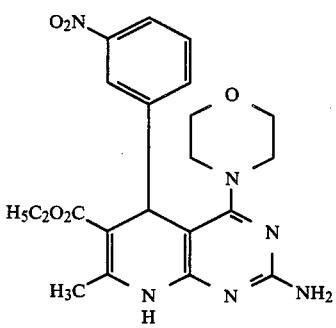

Analogously to Example 1, ethyl 2-amino-4-morpholino-7-methyl-5-(3-nitrophenyl)-5,8-dihydropyrido[2,3-d]pyrimidine-6-carboxylate of melting point: 208° C. (ethanol) was obtained by reacting ethyl 2-(3-nitrobenzylidene)-acetoacetate with 2,6-diamino-4-morpholino-pyrimidine in ethanol. Yield: 79%.

Example 53

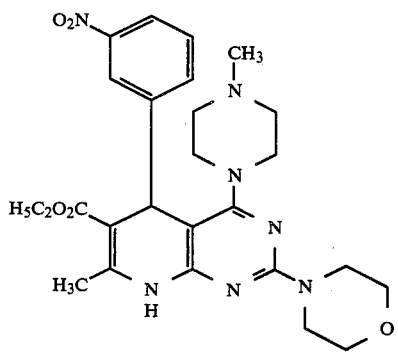

Analogously to Example 1, ethyl 2-morpholino-4-(N-4-methylpiperazin-1-yl)-7-methyl-5-(3-nitrophenyl)-5,8-dihydro-pyrido[2,3-d]pyrimidine-6-carboxylate of melting point: 218° C. (ethanol) was obtained by reacting ethyl 2-(3-nitrobenzyllidene)-acetoacetate with 6-amino-2-morpholino-4-(N-4-methylpiperazin-1-yl)-pyrimidine in ethanol. Yield: 77%.

Example 54

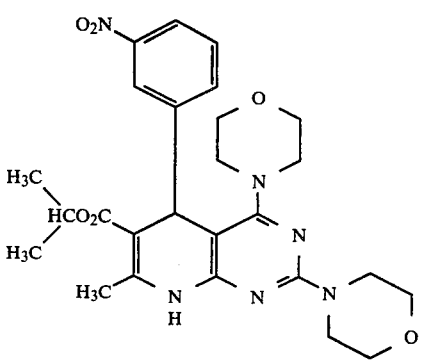

Analogously to Example 1, isopropyl 2,4-dimorpholino-7-methyl-5-(3-nitrophenyl)-5,8-dihydropyrido[2,3-d]pyrimidine-6-carboxylate of melting point: 229° C. (ethanol) was obtained by reacting isopropyl 2-(3-nitrobenzylidene)-acetoacetate with 6-amino-2,4-dimorpholino-pyrimidine in ethanol. Yield: 84%.

Example 55

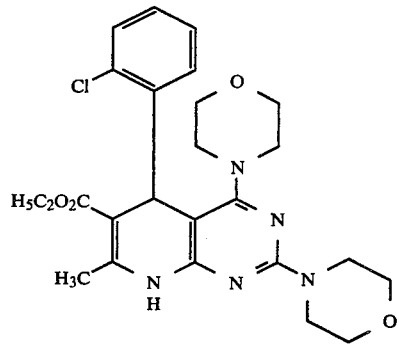

Analogously to Example 1, ethyl 2,4-dimorpholino-7-methyl-5-(2-chlorophenyl)-5,8-dihydro-pyrido[2,3-d]pyrimidine-6-carboxylate of melting point: 241° C. (ethanol) was obtained by reacting ethyl 2-(2-chlorobenzylidene)-acetoacetate with 6-amino-2,4-morpholino-pyrimidine in ethanol. Yield: 84%.

Example 56

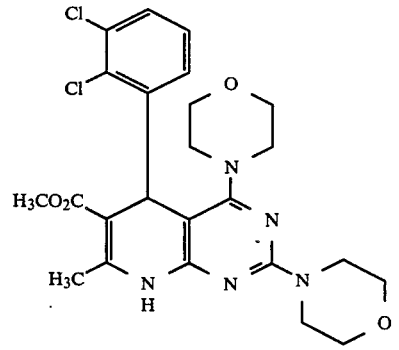

Analogously to Example 1, methyl 2,4-dimorpholino-7-methyl-5-(2,3-dichlorophenyl)-5,8-dihydro-pyrido[2,3-d]pyrimidine-6-carboxylate of melting point: 188° C. (ethanol) was obtained by reacting methyl 2-(2,3-dichlorobenzylidene)-acetoacetate with 6-amino-2,4-dimorpholino-pyrimidine in ethanol. Yield: 85%.

Example 57

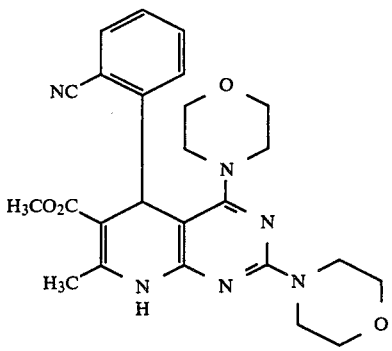

Analogously to Example 1, methyl 2,4-dimorpholino-7-methyl-5-(2-cyanophenyl)-5,8-dihydro-pyrido[2,3-d]pyrimidine-6-carboxylate of melting point: 221° C. (ethanol) was obtained by reacting methyl 2-(2-cyanobenzylidene)-acetoacetate with 6-amino-2,4-dimorpholino-pyrimidine in ethanol. Yield: 69%.

Example 58

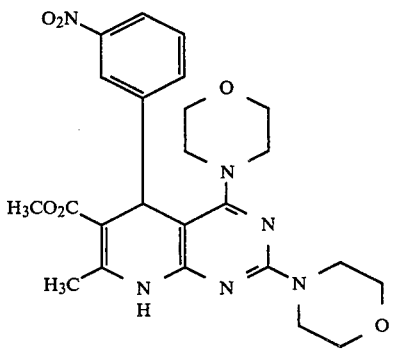

Analogously to Example 1, methyl 2,4-dimorpholino-7-methyl-5-(3-nitrophenyl)-5,8-dihydro-pyrido[2,3-d]pyrimidine-6-carboxylate of melting point: 165° C. (ethanol) was obtained by reacting methyl 2-(3-nitrobenzylidene)acetoacetate with 6-amino-2,4-dimorpholino-pyrimidine in ethanol. Yield: 86%.

Example 59

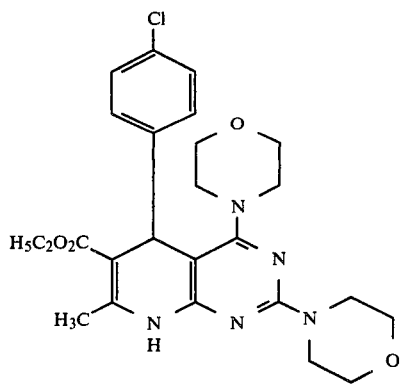

Analogously to Example 1, ethyl 2,4-dimorpholino-7-methyl-5-(4-chlorophenyl)-5,8-dihydro-pyrido[2,3-d]pyrimidine-6-carboxylate of melting point: 128° C. (isopropanol) was obtained by reacting ethyl 2-(4-chlorobenzylidene)-acetoacetate with 6-amino-2,4-dimorpholino-pyrimidine in ethanol. Yield: 65%.

Example 60

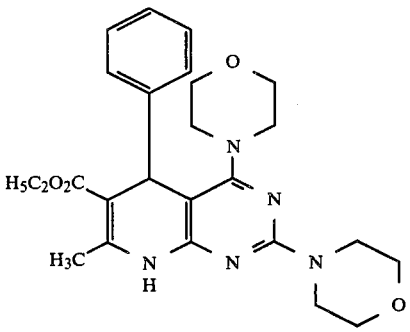

Analogously to Example 1, ethyl 2,4-dimorpholino-7-methyl-5-phenyl-5,8-dihydro-pyrido[2,3-d]pyrimidine-6-carboxylate of melting point: 178° C. (ethanol) was obtained by reacting ethyl 2-benzylidene-acetoacetate with 6-amino-2,4-dimorpholino-pyrimidine in ethanol. Yield: 82%.

Example 61

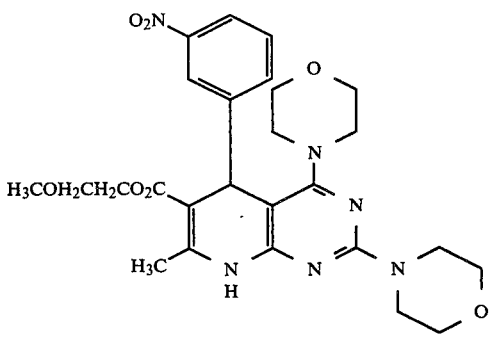

Analogously to Example 1, 2-methoxyethyl 2,4-dimorpholino-7-methyl-5-(3-nitrophenyl)-5,8-dihydropyrido[2,3-d]pyrimidine-6-carboxylate of melting point: 172° C. (ethanol) was obtained by reacting 2-methoxyethyl 2-(3-nitrobenzylidene)-acetoacetate with 6-amino-2,4-dimorpholino-pyrimidine in ethanol. Yield: 93%.

Example 62

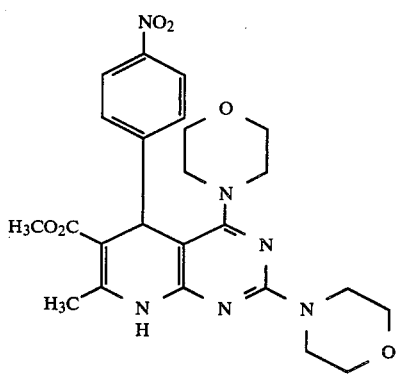

Analogously to Example 1, methyl 2,4-dimorpholino-7-methyl-5-(4-nitrophenyl)-5,8-dihydro-pyrido[2,3-d]pyrimidine-6-carboxylate of melting point: 236° C. (ethanol) was obtained by reacting methyl 2-(4-nitrobenzylidene)-acetoacetate with 6-amino-2,4-dimorpholino-pyrimidine in ethanol. Yield: 81%.

Example 63

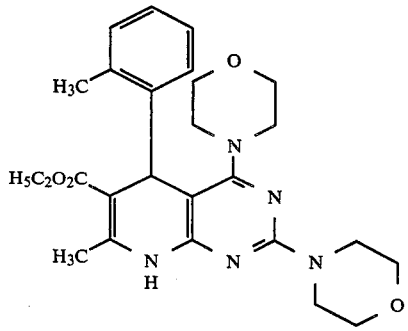

Analogously to Example 1, ethyl 2,4-dimorpholino-7-methyl-5-(2-methylphenyl)-5,8-dihydro-pyrido[2,3-d]pyrimidine-6-carboxylate of melting point: 234° C. (ethanol) was obtained by reacting ethyl 2-(2-methylbenzylidene)-acetoacetate with 6-amino-2,4-dimorpholino-pyrimidine in ethanol. Yield: 79%.

Example 64

Ethyl 2,4-dimorpholino-7-methyl-5-(3-cyanophenyl)-5,8-dihydro-pyrido[2,3-d]pyrimidine-6-carboxylate

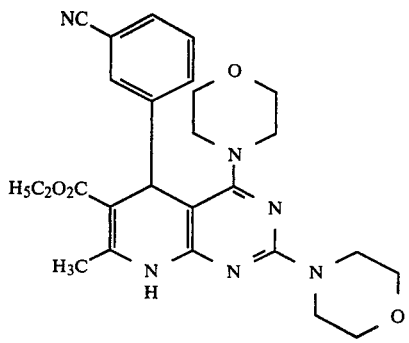

0.8 g (6 mmol) of 3-cyanobenzaldehyde, 0.8 g (6 mmol) of ethyl acetoacetate and 1.6 g (6 mmol) of 6-amino-2,4-dimorpholino-pyrimidine were heated together in 20 ml of ethanol for 15 hours under reflux. The reaction mixture was then cooled, and the precipitated product was filtered off with suction and recrystallized from a little ethanol, melting point: 210° C. Yield: 1.8 g (61%).

Example 65

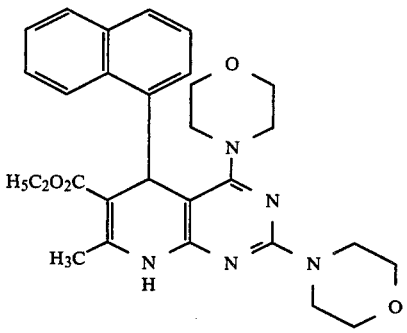

Analogously to Example 64, ethyl 2,4-dimorpholino-7-methyl-5-(naphth-1-yl)-5,8-dihydro-pyrido[2,3-d]pyrimidine-6-carboxylate of melting point: 198° C. (ethyl acetate) was obtained by reacting α-naphthylaldehyde, ethyl acetoacetate and 6-amino-2,4-dimorpholino-pyrimidine in ethanol. Yield: 58%.

Example 66

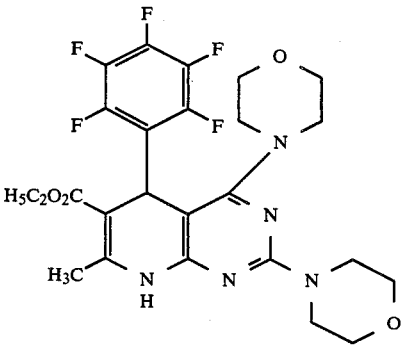

Analogously to Example 64, ethyl 2,4-dimorpholino-7-methyl-5-(pentafluorophenyl)-5,8-dihydro-pyrido[2,3-d]pyrimidine-6-carboxylate of melting point: 195° C. (ethanol) was obtained by reacting pentafluorobenzaldehyde, ethyl acetoacetate and 6-amino-2,4-dimorpholino-pyrimidine in ethanol. Yield: 65%.

Example 67

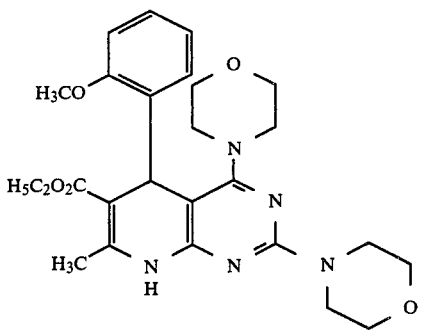

Analogously to Example 64, ethyl 2,4-dimorpholino-7-methyl-5-(2-methoxyphenyl)-5,8-dihydro-pyrido[2,3-d]pyrimidine-6-carboxylate of melting point: 188° C. (ethanol) was obtained by reacting 2-methoxybenzaldehyde, ethyl acetoacetate and 6-amino-2,4-dimorpholino-pyrimidine in ethanol. Yield: 81%.

Example 68

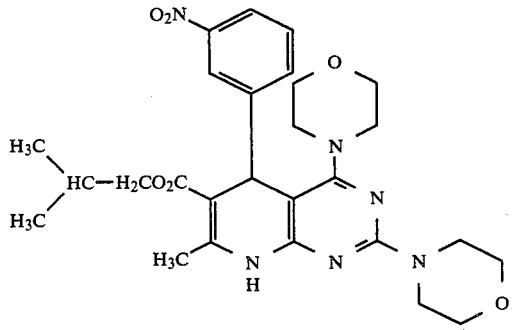

Analogously to Example 64, isobutyl 2,4-dimorpholino-7-methyl-5-(3-nitrophenyl)-5,8-dihydro-pyrido[2,3-d]pyrimidine-6-carboxylate of melting point: 214° C. (ethanol) was obtained by reacting 3-nitrobenzaldehyde, isobutyl acetoacetate and 6-amino-2,4-dimorpholino-pyrimidine in ethanol. Yield: 66%.

Example 69

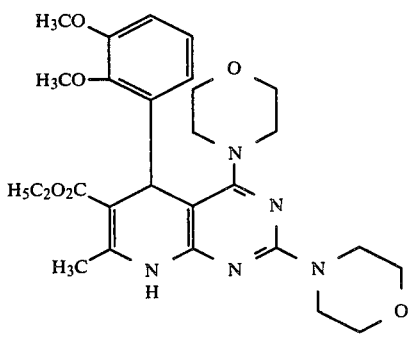

Analogously to Example 64, ethyl 2,4-dimorpholino-7-methyl-5-(2,3-dimethoxyphenyl)-5,8-dihydro-pyrido[2,3-d]pyrimidine-6-carboxylate of melting point: 194° C. (ethanol) was obtained by reacting 2,3-dimethoxybenzaldehyde, ethyl acetoacetate and 6-amino-2,4-dimorpholino-pyrimidine in ethanol. Yield: 57%.

Example 70

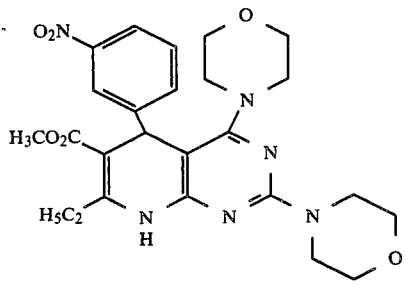

Analogously to Example 64, methyl 2,4-dimorpholino-7-ethyl-5-(3-nitrophenyl)-5,8-dihydro-pyrido[2,3-d]pyrimidine-6-carboxylate of melting point: 225° C. (chloroform/ethyl acetate) was obtained by reacting 3-nitrobenzaldehyde, methyl propionylacetate and 6-amino-2,4-dimorpholino-pyrimidine in ethanol. Yield: 51%.

Example 71

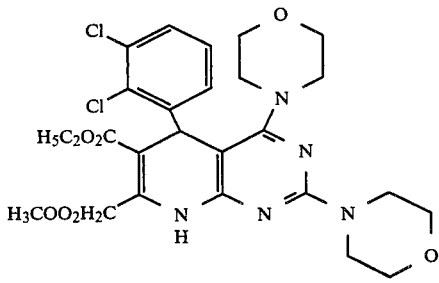

Analogously to Example 64, ethyl 2,4-dimorpholino-7-acetoxymethyl-5-(2,3-dichlorophenyl)-5,8-dihydro-pyrido[2,3-d]pyrimidine-6-carboxylate of melting point: 161° C. (chloroform/ethyl acetate) was obtained by reacting 2,3-dichlorobenzaldehyde, ethyl 4-acetoxyacetoacetate and 6-amino-2,4-dimorpholino-pyrimidine in ethanol. Yield: 47%.

Example 72

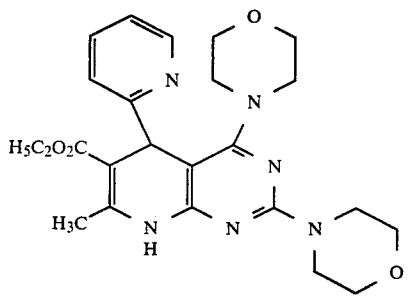

Analogously to Example 64, ethyl 2,4-dimorpholino-7-methyl-5-(pyrid-2-yl)-5,8-dihydro-pyrido[2,3-d]pyrimidine-6-carboxylate of melting point: 226° C. (ethanol/dimethylformamide) was obtained by reacting pyridine-2-aldehyde, ethyl acetoacetate and 6-amino-2,4-dimorpholino-pyrimidine in ethanol. Yield: 53%.

Example 73

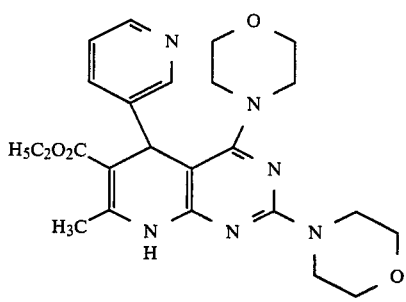

Analogously to Example 64, ethyl 2,4-dimorpholino-7-methyl-5-(pyrid-3-yl)-5,8-dihydro-pyrido[2,3-d]pyrimidine-6-carboxylate of melting point: 229° C. (ethanol) was obtained by reacting pyridine-3-aldehyde, ethyl acetoacetate and 6-amino-2,4-dimorpholino-pyrimidine in ethanol. Yield: 56%.

EXAMPLE 74

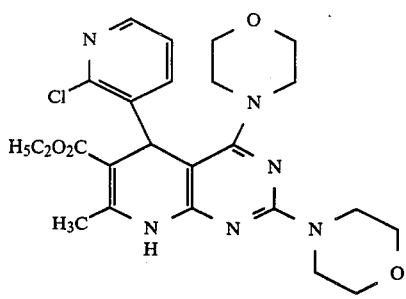

Analogously to Example 64, ethyl 2,4-dimorpholino-7-methyl-5-(2-chloro-pyrid-3-yl)-5,8-dihydro-pyrido[2,3-d]pyrimidine-6-carboxylate of melting point: 185° C. (ethyl acetate) was obtained by reacting 2-chloro-pyridine-3-aldehyde, ethyl acetoacetate and 6-amino-2,4-dimorpholino-pyrimidine in ethanol. Yield: 62%.

Example 75

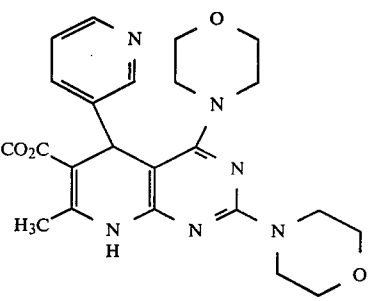

Analogously to Example 64, 2-acetoxyethyl 2,4-dimorpholino-7-methyl-5-(pyrid-3-yl)-5,8-dihydro-pyrido[2,3-d]pyrimidine-6-carboxylate of melting point: 170° C. (ethanol) was obtained by reacting by pyridine-3-aldehyde, 2-acetoxyethyl acetoacetate and 6-amino-2,4-dimorpholino-pyrimidine in isopropanol. Yield: 59%.

Example 76

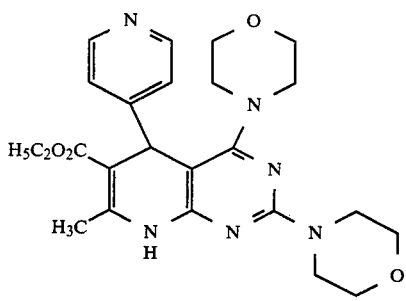

Analogously to Example 64, ethyl 2,4-dimorpholino-7-methyl-5-(pyrid-4-yl)-5,8-dihydro-pyrido[2,3-d]pyrimidine-6-carboxylate of melting point: 209° C. (toluene) was obtained by reacting pyridine-4-aldehyde, ethyl acetoacetate and 6-amino-2,4-dimorpholino-pyrimidine in ethanol. Yield: 53%.

Example 77

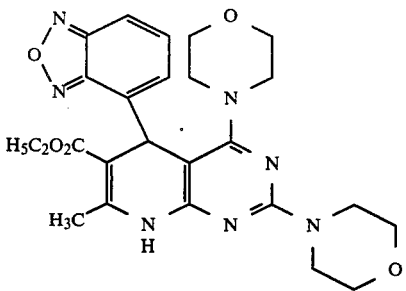

Analogously to Example 64, ethyl 2,4-dimorpholino-7-methyl-5-(2,1,3-benzoxadiazol-4-yl)-5,8-dihydro-pyrido[2,3-d]pyrimidine-6-carboxylate of melting point: 234° C. (ethyl acetate) was obtained by reacting 2,1,3-benzoxadiazol-4-aldehyde, ethyl acetoacetate and 6-amino-2,4-dimorpholino-pyrimidine in ethanol. Yield: 49%.

Example 78

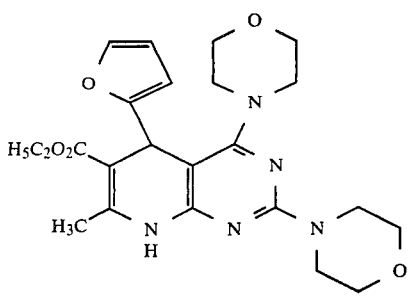

Analogously to Example 64, ethyl 2,4-dimorpholino-7-methyl-5-fur-2-yl)-5,8-dihydro-pyrido[2,3-d]pyrimidine-6-carboxylate of melting point: 172° C. (toluene) was obtained by reacting furan-2-aldehyde, ethyl acetoacetate and 6-amino-2,4-dimorpholino-pyrimidine in ethanol. Yield: 56%.

Example 79

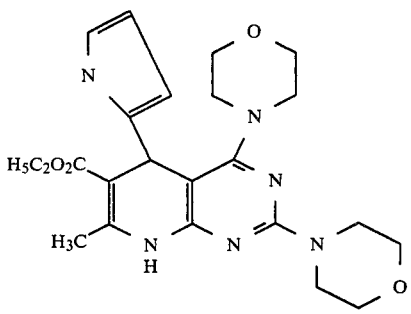

Analogously to Example 64, ethyl 2,4-dimorpholino-7-methyl-5-(thien-2-yl)-5,8-dihydro-pyrido[2,3-d]pyrimidine-6-carboxylate of melting point: 205° C. (ethyl acetate) was obtained by reacting thiophene-2-aldehyde, ethyl acetoacetate and 6-amino-2,4-dimorpholino-pyrimidine in ethanol. Yield: 43%.

Example 80

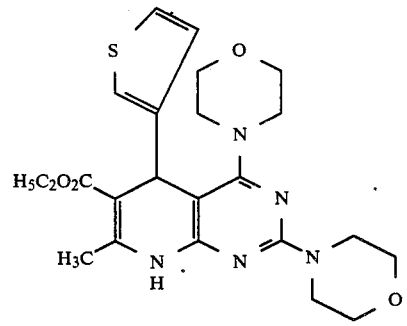

Analogously to Example 64, ethyl 2,4-dimorpholino-7-methyl-5-(thien-3-yl)-5,8-dihydro-pyrido[2,3-d]pyrimidine-6-carboxylate of melting point: 208° C. (ethanol) was obtained by reacting thiophene-3-aldehyde, ethyl acetoacetate and 6-amino-2,4-dimorpholino-pyrimidine in ethanol. Yeild: 69%.

It will be appreciated that the instant specification and examples are set forth by way of illustration and not limitation, and that various modifications and changes may be made without departing from the spirit and scope of the present invention.

We claim:

1. A pyridopyrimidine of the formula

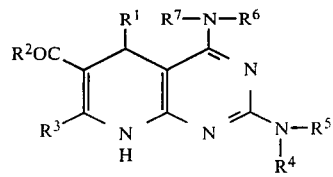

in which $R^1$ represents carbocyclic aryl or a heterocyclic radical from the group consisting of thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzthiadiazolyl, quinolyl, isoquinolyl, quinazolyl and quinoxalyl, the aryl radical and the heterocyclic radicals optionally containing 1 to 5 identical or different substituents from the group consisting of phenyl, alkyl, alkoxy, alkylene, dioxyalkylene, halogen, polyfluoroalkyl, polyfluoroalkoxy, alkylamino, nitro, cyano, azido, alkoxycarbonyl, carbamoyl, sulphamoyl, $SO_m$-alkyl (m=0 to 2) and $SO_m$-aralkyl (m=0 to 2), $R^2$ represents a straight-chain, branched or cyclic alkyl radical or an aryl or aralkyl group, or denotes an amino, monoalkylamino or dialkylamino group, it being possible for the alkyl groups to be optionally substituted by a phenyl radical, or represents an anilino radical optionally substituted by alkyl, alkoxy or halogen, or represents the radical $OR^8$, in which $R^8$ represents a straight-chain, branched or cyclic, saturated or unsaturated hydrocarbon radical which is optionally interrupted by an oxygen or sulphur atom in the chain and/or is optionally substituted by halogen, cyano, hydroxyl, acyloxy, nitro, nitrooxy, alkoxycarbonyl, phenyl, phenoxy, phenylthio, phenylsulphonyl, pyridyl or an amino group, this amino group being optionally substituted by two identical or different substituents from the group consisting of alkyl, alkoxyalkyl, aryl and aralkyl, or the amino group optionally being substituted in such a way that 2 substituents, together with the nitrogen atom, form a 5-membered to 7-membered ring which can contain oxygen or sulphur as a further hetero-atom or an N-alkyl/phenyl grouping, $R^3$ represents hydrogen, a straight-chain, branched or cyclic hydrocarbon radical optionally substituted by 1 or 2 alkoxy or acyloxy groups, or an aryl or aralkyl radical, and $R^4$, $R^5$, $R^6$ and $R^7$, which can be identical or different, represent hydrogen or a straight-chain or branched alkyl radical optionally substituted by hydroxyl, alkoxy, or acyloxy, it being possible for the radicals $R^4$ and $R^5$ and/or $R^6$ and $R^7$, together with the respective nitrogen atom, to form a 5-membered to 7-membered ring which optionally contains oxygen or sulphur as a further hetero-atom or an N-alkyl or N-aryl grouping, or represents an aryl or aralkyl radical.

2. A compound according to claim 1, in which $R^1$ represents a phenyl or naphthyl radical or thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzthiadiazolyl, quinolyl, isoquinolyl, quinazolyl or quinoxalyl, it being possible for the heterocyclic radicals mentioned and the phenyl radical and the naphthyl radical each to carry 1 to 5 identical or different substituents, for which phenyl, straight-chain or branched alkyl having up to 8 carbon atoms, cycloalkyl having 3 to 7 carbon atoms, alkenyl or alkinyl having 2 to 6 carbon atoms, alkoxy having 1 to 4 carbon atoms, alkenoxy and alkinoxy having 2 to 6 carbon atoms, tri-, tetra- and penta-methylene, dioxymethylene, dioxyethylidene, fluorine, chloroine, bromine or iodine, trifluoromethyl, trifluoroethyl, trifluoromethoxy, difluoromethoxy, tetrafluoroethoxy, dialkylamino having 1 to 4 C atoms, nitro, cyano, azido, alkoxycarbonyl having 1 to 4 C atoms in the alkoxy radical, carbamoyl, N,N-dimethylcarbamoyl, sulphamoyl, $SO_m$-alkyl, in which m denotes 0 to 2 and alkyl contains 1 to 4 carbon atoms, or $SO_m$-benzyl with m=0 to 2 may be mentioned as substituents, $R^2$ represents a straight-chain, branched or cyclic alkyl radical having up to 8 carbon atoms, or the phenyl or benzyl group or represents the amino, monoamino or dialkylamino group having up to 4 carbon atoms per alkyl group, it being possible for one or both alkyl groups to be substituted by a phenyl radical, or represents the anilino radical optionally substituted by fluorine or chlorine or by alkyl or alkoxy having 1 to 4 carbon atoms, or represents the radical $OR^8$, in which $R^8$ represents a straight-chain, branched or cyclic, saturated or unsaturated hydrocarbon radical which has up to 12 carbon atoms and is optionally interrupted by 1 oxygen or sulphur atom in the chain and/or is optionally substituted by halogen, cyano, hydroxyl, acetoxy, benzoyloxy, nitro, nitrooxy, alkoxycarbonyl having up to 4 carbon atoms in the alkoxy group, phenyl, phenoxy, phenylthio, phenylsulphonyl, α-, β- or γ-pyridyl or an amino group, this amino group optionally carrying one or two identical or different substituents from the group consisting of alkyl having 1 to 4 carbon atoms, alkoxyalkyl having up to 6 carbon atoms, phenyl, benzyl or phenethyl, or the nitrogen of this amino group, together with the substituents, optionally forming a 5-membered to 7-membered ring which can contain an oxygen or sulphur atom as a further hetero-atom or an N-phenyl group or an N-alkyl group having 1 to 4 carbon atoms in the alkyl radical, $R^3$ represents hydrogen or represents a straight-chain, branched or cyclic hydrocarbon radical which has up to 6 carbon atoms and is optionally substituted by 1 or 2 akoxy groups having 1 to 4 carbon atoms or by an acetoxy or benzoyloxy group, or represents a phenyl radical or a benzyl radical, and $R^4$, $R^5$, $R^6$ and $R^7$ are identical or different and each represent hydrogen or represent a straight-chain or branched alkyl radical which is up to 8 carbon atoms and is optionally substituted by hydroxyl, methoxy, acetoxy or benzoyloxy, it being possible for the radicals $R^4$ and $R^5$ and/or $R^6$ and $R^7$, together with the respective nitrogen atom, to form a 5-membered to 7-membered ring which optionally contains, as a further hetero-atom, oxygen or sulphur or an N-alkyl group having up to 4 carbon atoms or an N-phenyl group, or represent a phenyl or benzyl radical.

3. A compound according to claim 1, in which $R^1$ represents a phenyl or naphthyl radical or thienyl, furyl, pyridyl, pyridazinyl, pyrimidyl, benzoxadiazolyl, benzthiadiazolyl, quinolyl or isoquinolyl, it being possible for the said heterocyclic radicals and for the phenyl and naphthyl radical to carry 1 to 5 identical or different substituents from the group consisting of straight-chain or branched alkyl having up to 8 carbon atoms, alkoxyalkyl having 1 to 4 carbon atoms, dioxymethylene, fluoro, chloro, bromo, trifluoromethyl, trifluoromethoxy, difluoromethoxy, nitro, cyano, azido, thioalkyl, sulphonylalkyl each having 1 to 4 C atoms in the alkyl radical, thiobenzyl and sulphonylbenzyl, $R^2$ represents alkyl having up to 8 C atoms, phenyl or benzyl, or represents the radical $OR^8$, in which $R^8$ represents a straight-chain, branched or cyclic, saturated or unsaturated hydrocarbon radical which has up to 12 carbon atoms and is optionally interrupted by 1 oxygen or sulphur atom in the chain and/or is optionally substituted by halogen, cyano, hydroxyl, acetoxy, phenyl, phenoxy, phenylthio, α-, β- or γ-pyridyl or an amino group, this amino group optionally carrying one or two identical or different substituents from the group consisting of alkyl having 1 to 4 C atoms, phenyl and benzyl, $R^3$ represents a straight-chain or branched hydrocarbon radical which has up to 6 C atoms and is optionally substituted by 1 or 2 alkoxy groups having 1 to 4 C atoms or by an acetoxy group, or represents a phenyl radical or benzyl radical and $R^4$, $R^5$, $R^6$ and $R^7$ each are identical or different and represent hydrogen or a straight-chain or branched alkyl radical which has up to 8 carbon atoms and is optionally substituted by hydroxyl, methoxy or acetoxy, it being possible for the radicals $R^4$ and $R^5$ and/or $R^6$ and $R^7$, together with the respective nitrogen atom, to form a 5-membered to 7-membered ring which optionally contains, as a further hetero-actom, oxygen, sulphur or an N-alkyl group having up to 4 C atoms or an N-phenyl group.

4. A compound according to claim 1 wherein such compound is ethyl 2,4-dimorpholino-7-methyl-5-(pyrid-2-yl)-5,8-dihydropyrido[2,3-d]pyrimidine-6-carboxylate of the formula

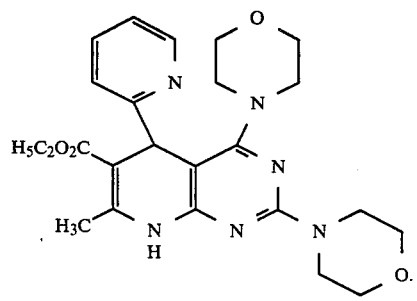

5. A compound according to claim 1 wherein such compound is ethyl 2,4-dimorpholino-7-methyl-5-(pyrid- 3-yl)-5,8-dihydropyrido[2,3-d]pyrimidine-6-carboxylate of the formula

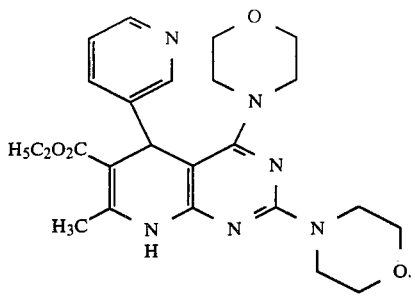

6. A compound according to claim 1 wherein such compound is ethyl 2,4-dimorpholino-7-methyl-5-(2-chloro-pyrid-3-yl)-5,8-dihydro-pyrido[2,3-d]pyrimidine-6-carboxylate of the formula

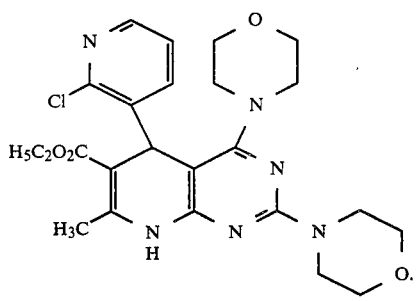

7. A compound according to claim 1 wherein such compound is 2-acetoxyethyl 2,4-dimorpholino-7-methyl-5-(pyrid-3-yl)-5,8-dihydro-pyrido-[2,3-d]pyrimidine-6-carboxylate of the formula

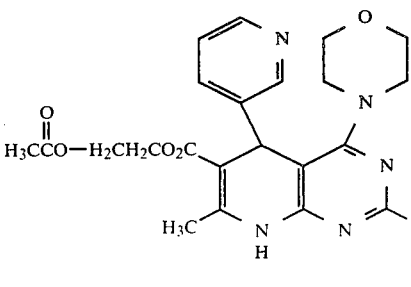

8. A compound according to claim 1 wherein such compound is ethyl 2,4-dimorpholino-7-methyl-5-(2,1,3-benzoxadiazol-4-yl)-5,8-dihydro-pyrido-[2,3-d]pyrimidine-6-carboxylate of the formula

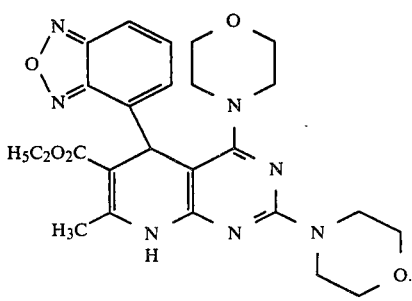

9. A circulation active composition comprising a circulation active effective amount of a compound according to claim 1 in admixture with a pharmaceutically acceptable diluent.

10. A unit dose of a composition according to claim 9, in the form of a tablet, capsule or ampule.

11. A method of treating the circulation problems of a patient in need thereof which comprises administering to such patient an amount effective therefor of a compound according to claim 1.

12. The method according to claim 11, wherein such compound is
 ethyl 2,4-dimorpholine-7-methyl-5-(pyrid-2-yl)-5,8-dihydro-pyrido[2,3-d]pyrimidine-6-carboxylate,
 ethyl 2,4-dimorpholino-7-methyl-5-(pyrid-3-yl)-5,8-dihydro-pyrido[2,3-d]pyrimidine-6-carboxylate,
 ethyl 2,4-dimorpholino-7-methyl-5-(2-chloro-pyrid-3-yl)-5,8-dihtdro-pyrido[2,3-d]pyrimidine-6 -carboxylate,
 2-acetoxyethyl 2,4-dimorpholino-7-methyl-5-(pyrid-3-yl)-5,8-dihydro-pyrido-[2,3-d]pyrimidine-6-carboxylate or
 ethyl 2,4-dimorpholino-7-methyl-5-(2,1,3-benzoxadiazol-4-yl)-5,8-dihydro-pyrido-[2,3-d]pyrimidine-6-carboxylate.

* * * * *